(12) United States Patent
Krohn et al.

(10) Patent No.: US 11,998,629 B2
(45) Date of Patent: *Jun. 4, 2024

(54) METHOD FOR DYEING KERATINOUS MATERIAL, COMPRISING THE USE OF AN ORGANOSILICON COMPOUND, AN EFFECT PIGMENT AND A FILM-FORMING POLYMER

(71) Applicant: Henkel AG & Co. KGaA, Duesseldorf (DE)

(72) Inventors: Rene Krohn, Norderstedt (DE); Thomas Hippe, Appen (DE); Stefan Hoepfner, Hamburg (DE); Jessica Brender, Hamburg (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/762,027

(22) PCT Filed: Aug. 25, 2020

(86) PCT No.: PCT/EP2020/073677
§ 371 (c)(1),
(2) Date: Mar. 18, 2022

(87) PCT Pub. No.: WO2021/052720
PCT Pub. Date: Mar. 25, 2021

(65) Prior Publication Data
US 2022/0339089 A1    Oct. 27, 2022

(30) Foreign Application Priority Data
Sep. 18, 2019 (DE) .......... 102019214205.2

(51) Int. Cl.
| | |
|---|---|
| A61Q 5/10 | (2006.01) |
| A61K 8/02 | (2006.01) |
| A61K 8/26 | (2006.01) |
| A61K 8/29 | (2006.01) |
| A61K 8/365 | (2006.01) |
| A61K 8/58 | (2006.01) |
| A61K 8/81 | (2006.01) |

(52) U.S. Cl.
CPC ............ *A61K 8/585* (2013.01); *A61K 8/0262* (2013.01); *A61K 8/26* (2013.01); *A61K 8/29* (2013.01); *A61K 8/365* (2013.01); *A61K 8/8158* (2013.01); *A61K 8/8176* (2013.01); *A61Q 5/10* (2013.01); *A61K 2800/436* (2013.01); *A61K 2800/884* (2013.01); *A61K 2800/95* (2013.01)

(58) Field of Classification Search
CPC ........ A61K 8/585; A61K 8/0262; A61K 8/26; A61K 8/29; A61K 8/365; A61K 8/8158; A61K 8/8176; A61K 2800/436; A61K 2800/884; A61K 2800/95; A61K 2800/43; A61Q 5/10; A61Q 5/065
USPC ............................................. 8/405
See application file for complete search history.

(56) References Cited

U.S. PATENT DOCUMENTS

| | | | | |
|---|---|---|---|---|
| 2010/0083446 A1* | 4/2010 | Brun | ...................... | A61K 8/891 8/405 |
| 2015/0080338 A1* | 3/2015 | Lorant | ................... | A61Q 19/00 514/63 |
| 2015/0313814 A1 | 11/2015 | Lawson et al. | | |

FOREIGN PATENT DOCUMENTS

| | | |
|---|---|---|
| EP | 2168633 A2 | 3/2010 |
| EP | 3081601 A1 | 10/2016 |
| WO | 2005075578 A2 | 8/2005 |
| WO | 2013068979 A2 | 5/2013 |
| WO | 2018130912 A1 | 7/2018 |

* cited by examiner

*Primary Examiner* — Eisa B Elhilo
(74) *Attorney, Agent, or Firm* — Lorenz & Kopf, LLP

(57) ABSTRACT

A method and a kit-of-parts are provided for dyeing keratinous material. The method includes applying a first agent to the keratinous material and applying an second agent to the keratinous material. The first agent includes at least one organic silicon compound. The second agent comprises at least one colorant compound and at least one film-forming polymer. The colorant compound includes at least one effect pigment including a substrate platelet including synthetic mica. The colorant compound further includes a coating including at least a first metal oxide (hydrate) layer.

14 Claims, No Drawings

METHOD FOR DYEING KERATINOUS MATERIAL, COMPRISING THE USE OF AN ORGANOSILICON COMPOUND, AN EFFECT PIGMENT AND A FILM-FORMING POLYMER

CROSS-REFERENCE TO RELATED APPLICATION

This application is a U.S. National-Stage entry under 35 U.S.C. § 371 based on International Application No. PCT/EP2020/073677, filed Aug. 25, 2020, which was published under PCT Article 21(2) and which claims priority to German Application No. 102019214205.2, filed Sep. 18, 2019, which are all hereby incorporated in their entirety by reference.

TECHNICAL FIELD

The subject of the present application is a process for dyeing keratinous material, in particular human hair, which comprises the application of two different agents (a), and (b). The agent (a) comprises at least one organic silicon compound. The agent (b) comprises at least one color-imparting compound (b1) comprising at least one selected effect pigment, and a film-forming polymer (b2).

A second subject of this application is a multi-component packaging unit (kit-of-parts) for dyeing keratinous material, in particular human hair, which comprises agent (a) and (b) separately assembled in two different containers.

BACKGROUND

Changing the shape and color of keratinous material, especially of human hair, represents an important area of modern cosmetics. To change the color of the hair, the professional knows various coloring systems, depending on the requirements of coloring. For permanent, intensive dyeings with good fastness properties and good gray coverage, oxidation dyes are usually used. Such colorants contain oxidation dye precursors, so-called developer components and coupler components, which form the actual dyes under the influence of oxidizing agents such as hydrogen peroxide among themselves. Oxidation dyes are exemplified by very long-lasting dyeing results.

When using direct dyes, already formed dyes diffuse from the colorant into the hair fiber. Compared to oxidative hair dyeing, the dyeings obtained with direct dyes have lower durability and faster washout. Dyes with direct dyes usually remain on the hair for a period of between 5 and 20 washes.

The use of color pigments is known for short-term color changes on the hair and/or skin. Color pigments are generally understood to be insoluble, color-imparting substances. These are present undissolved in the form of small particles in the coloring formulation and are merely deposited externally on the hair fibers and/or the skin surface. Therefore, they can usually be removed without residue by a few washes with surfactant-comprising cleaning agents. Various products of this type are available on the market under the name of hair mascara.

If the user desires a particularly long-lasting coloring of his hair, the use of oxidative dyes is his only option so far. However, despite multiple optimization attempts, an unpleasant ammonia odor or amine odor cannot be completely avoided during oxidative hair coloring. The hair damage still associated with the use of the oxidative dyes also has a detrimental effect on the user's hair. A continuing challenge is therefore the search for alternative, high-performance dyeing processes.

EP 2168633 B1 deals with the task of producing long-lasting hair colorations using pigments. The paper teaches that when a combination of pigment, organic silicon compound, hydrophobic polymer and a solvent is used on hair, it is possible to create colorations that are said to be particularly resistant to shampooing.

Metallic luster pigments or metallic effect pigments are widely used in many fields of technology. They are used, for example, for coloring coatings, printing inks, inks, plastics, glasses ceramic products and preparations of decorative cosmetics such as nail polish. They are exemplified above all by their attractive angle-dependent color impression (goniochromism) and their metallic-looking luster.

BRIEF SUMMARY

A method is provided for dyeing keratinous material and includes applying a first agent to the keratinous material and applying an second agent to the keratinous material. The first agent includes at least one organic silicon compound. The second agent comprises at least one colorant compound and at least one film-forming polymer. The colorant compound includes at least one effect pigment including a substrate platelet including synthetic mica. The colorant compound further includes a coating including at least a first metal oxide (hydrate) layer.

Further, a multi-component packaging unit (kit-of-parts) is provided for dyeing keratinous material, comprising separately assembled a first container comprising an agent (a), wherein the agent (a) comprises at least one organic silicon compound (a1) and, optionally, at least one coloring compound (a2), a second container containing an agent (b), wherein the agent contains (b): (b1) at least one colorant compound comprising at least one effect pigment comprising a substrate platelet comprising synthetic mica, and a coating comprising at least a first metal oxide (hydrate) layer, and (b2) at least one film-forming polymer.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Hair with a metallic finish or metallic highlights is in trend. The metallic tone makes the hair look thicker and shinier.

Effect pigments based on metal-comprising substrate platelets have only limited stability in an aqueous medium. For example, aluminum-based effect pigments decompose comparatively rapidly in water to form hydrogen and aluminum hydroxide.

There is a need to provide hair dyes with effect pigments that on the one hand have high wash and rub fastness and on the other hand do not negatively affect hair properties such as manageability and feel. For this purpose, it would be desirable if the effect pigments used had a high covering power and could be applied to the hair in thin layers. The effect pigments used should also be stable in storage over a long period of time, insensitive to corrosion in the event of prolonged contact with water.

Accordingly, the task of the present disclosure was to provide a coloring system with effect pigments that has fastness properties comparable to oxidative coloring. In particular, the wash fastness properties should be outstanding, but the use of the oxidation dye precursors normally used for this purpose should be avoided.

Surprisingly, it has now been found that the task can be excellently solved if keratinous materials, in particular human hair, are colored by a process in which at least two agents (a) and (b) are applied to the keratinous materials (hair). In this case, the agent (a) comprises at least one organic Silicon compound, and the agent (b) comprises at least one selected effect pigment (b1) and a film-forming polymer (b2).

When using the two agents (a) and (b) in a dyeing process, keratinous material could be dyed with particularly high color intensity and high fastness properties.

A first object of the present disclosure is a method for coloring keratinous material, in particular human hair, comprising the following steps:
  Application of an agent (a) to the keratinous material, the agent (a) comprising at least one organic silicon compound, and
  Application of an agent (b) to the keratinous material, wherein the agent (b) comprises:
(b1) at least one colorant compound comprising at least one effect pigment comprising α) a substrate platelet comprising synthetic mica, and ß) a coating comprising at least a first metal oxide (hydrate) layer, and
(b2) at least one film-forming polymer.

The use of synthetic mica (fluorphlogopite) has several advantages over the traditional natural mica flakes often used in effect pigments. Thus, substrate platelets made of synthetic mica have lower heavy metal and impurity contents than natural mica. Also, synthetic mica substrate platelets have a smooth, uniform surface that leads to more uniform deposition of coating materials, especially metal oxide (hydrates), and thus to high color purity and reliability. Compared to effect pigments with metal-comprising substrate platelets, the effect pigments based on synthetic mica have the advantage of corrosion resistance, which leads to higher storage stability when the effect pigments are mixed with water and to more degrees of freedom in the formulation of the agent (b).

Keratinous Material

Keratinous material means hair, the skin, the nails (such as fingernails and/or toenails). Furthermore, wool, fur and feathers also fall under the definition of keratinous material.

Preferably, keratinous material is understood to mean human hair, human skin and human nails, in particular fingernails and toenails. Very preferably, keratinous material is understood to mean human hair.

Agents (a) and (b)

In the process, agents (a) and (b) are applied to the keratinous material, in particular human hair. The two agents (a) and (b) are different from each other.

Accordingly, a method for dyeing keratinous material, in particular human hair, is disclosed, comprising the following steps:
  Application of an agent (a) to the keratinous material, the agent (a) comprising at least one organic silicon compound, and
  Application of an agent (b) to the keratinous material, wherein the agent (b) comprises:
(b1) at least one colorant compound comprising at least one effect pigment comprising α) a substrate platelet comprising synthetic mica, and ß) a coating comprising at least a first metal oxide (hydrate) layer, and
(b2) and at least one film-forming polymer,
the two agents (a) and (b) being different from each other.

Agent (a)

Agent (a) is exemplified by its content of at least one organic silicon compound, in particular at least one organic silane. The organic silicon compounds or organic silanes included in agent (a) is reactive compounds.

Agent (a) comprises the organic silicon compound(s), in particular the organic silane(s), in a cosmetic carrier which may be water-comprising, water-poor or even water-free. In addition, the cosmetic carrier can be liquid, gel-like, creamy, pasty, powdery or even solid (e.g., in the form of a tablet or a pressed product). Preferably, the cosmetic carrier of agent (a) is an aqueous or aqueous-alcoholic carrier. For hair coloring, such carriers are, for example, creams, emulsions, gels or also surfactant-comprising foaming solutions, such as shampoos, foam aerosols, foam formulations or other preparations suitable for application to the hair.

The cosmetic carrier is preferably water-comprising, which means that the carrier comprises at least 2% by weight of water, based on its weight. Preferably, the water content is above 5% by weight, more preferably above 10% by weight even more preferably above 15% by weight. The cosmetic carrier can also be aqueous-alcoholic. For the purposes of the present disclosure, aqueous alcoholic solutions are understood to mean aqueous solutions comprising 2 to 70% by weight of a $C_1$-$C_4$ alcohol, in particular ethanol or isopropanol. The agents may additionally contain other organic solvents, such as methoxy butanol, benzyl alcohol, ethyl diglycol or 1,2-propylene glycol. Preferred solvents are all water-soluble organic solvents.

The term "coloring agent" is used in the context of the present disclosure to refer to a coloring of keratinous material, in particular human hair, brought about using pigments and/or direct dyes. During this coloring process, the coloring compounds are deposited in a particularly homogeneous and smooth film on the surface of the keratinous material or diffuse into the keratinous fiber. The film is formed in situ by oligomerization or polymerization of the organic Silicon compounds, as well as by the interaction of organic silicon compound with the coloring compounds.

Organic Silicon Compounds

As an essential component of the present disclosure, the agent (a) comprises at least one organic silicon compound (a1). Preferred organic silicon compounds (a1) are selected from silanes having one, two or three silicon atoms.

Organic silicon compounds, alternatively referred to as organosilicon compounds, are compounds that either have a direct silicon-carbon (Si—C) bond or in which the carbon is attached to the silicon atom via an oxygen, nitrogen or sulfur atom. The organic silicon compounds are preferably compounds comprising one to three silicon atoms. Particularly preferably, the organic silicon compounds contain one or two silicon atoms. The agent (a) particularly preferably comprises at least one organic silicon compound (a1) selected from silanes having one, two or three silicon atoms.

According to the IUPAC rules, the term silane stands for a substance group of chemical compounds based on a silicon backbone and hydrogen. In organic silanes, the hydrogen atoms are wholly or partially replaced by organic groups such as (substituted) alkyl groups and/or alkoxy groups. In the organic silanes, some of the hydrogen atoms may also be replaced by hydroxy groups.

In a particularly preferred embodiment, the method is exemplified by the application of an agent (a) to the keratinous material, wherein the agent (a) comprises at least one organic silicon compound selected from silanes having one, two or three silicon atoms.

The agent (a) particularly preferably comprises at least one organic silicon compound selected from silanes having one, two or three silicon atoms, the organic silicon compound further comprising one or more basic chemical functions and one or more hydroxyl groups or hydrolysable groups per molecule.

In a particularly preferred embodiment, the method is exemplified by the application of an agent (a) to the keratinous material, said agent (a) comprising at least one organic silicon compound (a1) selected from silanes having one, two or three silicon atoms, said organic silicon compound further comprising one or more basic chemical functions and one or more hydroxyl groups or hydrolysable groups per molecule.

This basic group can be, for example, an amino group, an alkylamino group, a dialkylamino group or a trialkylamino group, which is preferably connected to a silicon atom via a linker. Preferably, the basic group is an amino group, a $C_1$-$C_6$-alkylamino group or a di($C_1$-$C_6$)-alkylamino group.

The hydrolysable group(s) is preferably a $C_1$-$C_6$ alkoxy group, in particular an ethoxy group or a methoxy group. It is preferred if the hydrolysable group is directly bonded to the silicon atom. For example, if the hydrolysable group is an ethoxy group, the organic silicon compound preferably comprises a structural unit R'R''R'''Si—O—$CH_2$—$CH_3$. The residues R', R'' and R''' represent the three remaining free valencies of the silicon atom.

A very particularly preferred method is wherein the agent (a) comprises at least one organic silicon compound selected from silanes having one, two or three silicon atoms, the organic silicon compound preferably comprising one or more basic chemical functions and one or more hydroxyl groups or hydrolysable groups per molecule.

Particularly good results were obtained when the agent (a) comprises at least one organic silicon compound (a1) of the formula (I) and/or (II).

In another very particularly preferred embodiment, a process is wherein an agent (a) is applied to the keratinous material or human hair, the agent (a) comprising at least one organic silicon compound (a1) of the formula (I) and/or (II),

$$R_1R_2N\text{-}L\text{-}Si(OR_3)_a(R_4)_b \qquad (I),$$

where
$R_1$, R2 independently of one another represent a hydrogen atom or a $C_1$-$C_6$-alkyl group,
L stands for a linear or branched divalent $C_1$-$C_{20}$-alkylene group,
R3 represents a hydrogen atom or a $C_1$-$C_6$-alkyl group,
R4 represents a $C_1$-$C_6$-alkyl group
a, represents an integer from 1 to 3, and
b stands for the integer 3–a,

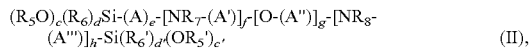

$$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \qquad (II),$$

where
R5, R5', R5'' independently represent a hydrogen atom or a C1-C6-alkyl group,
R6, R6' and R6'' independently represent a $C_1$-$C_6$-alkyl group,
A, A', A'', A''' and A'''' independently represent a linear or branched divalent $C_1$-$C_{20}$-alkylene group,
R7 and $R_8$ independently represent a hydrogen atom, a $C_1$-$C_6$-alkyl group, a hydroxy-$C_1$-$C_6$-alkyl group, a C2-$C_6$-alkenyl group, an amino-$C_1$-$C_6$-alkyl group or a group of the formula (III) are

$$(A'''')\text{-}Si(R_6'')_{d''}(OR_5'')_{c''} \qquad (III),$$

c, stands for an integer from 1 to 3,
d stands for the integer 3–c,
c' stands for an integer from 1 to 3,
d' stands for the integer 3–c',
c'' stands for an integer from 1 to 3,
d'' stands for the integer 3–c'',
e stands for 0 or 1,
f stands for 0 or 1,
g stands for 0 or 1,
h stands for 0 or 1,
with the provision that at least one of the residues from e, f, g and h is different from 0.

The substituents $R_1$, $R_2$, $R_3$, $R_4$, $R_5$, $R_{5'}$, $R_{5''}$, $R_6$, $R_6'$, $R_6''$, $R_7$, $R_8$, L, A, A', A'', A''' and A'''' in the compounds of formula (I) and (II) are exemplified below:

Examples of a $C_1$-$C_6$-alkyl group include methyl, ethyl, propyl, isopropyl, n-butyl, s-butyl and t-butyl, n-pentyl and n-hexyl groups. Propyl, ethyl and methyl are preferred alkyl radicals. Examples for a C2-$C_6$-Alkenyl group are vinyl, allyl, but-2-enyl, but-3-enyl as well as isobutenyl, preferred C2-$C_6$-Alkenyl radicals are vinyl and allyl. Preferred examples of a hydroxy-$C_1$-$C_6$-alkyl group include a hydroxymethyl, a 2-hydroxyethyl, a 2-hydroxypropyl, a 3-hydroxypropyl, a 4-hydroxybutyl, a 5-hydroxypentyl and a 6-hydroxyhexyl group; a 2-hydroxyethyl group is particularly preferred. Examples of an amino-$C_1$-$C_6$-alkyl group are the aminomethyl group, the 2-aminoethyl group, the 3-aminopropyl group. The 2-aminoethyl group is particularly preferred. Examples of a linear divalent $C_1$-C20-alkylene group are, for example, the methylene group (—CH2-), the ethylene group (—CH2-CH2-), the propylene group (—CH2-CH2-CH2-) and the butylene group (—CH2-CH2-CH2-CH2-). The propylene group (—CH2-CH2-CH2-) is particularly preferred. From a chain length of 3 C atoms, divalent alkylene groups can also be branched. Examples of branched, divalent $C_3$-$C_{20}$-alkylene groups are (—$CH_2$—CH($CH_3$)—) and (—CH2-CH($CH_3$)—$CH_2$—).

In the organic silicon compounds (a1) of the formula (I)

$$R_1R_2N\text{-}L\text{-}Si(OR_3)_a(R_4)_b \qquad (I),$$

the radicals $R_1$ and $R_2$ independently of one another represent a hydrogen atom or a C1-$C_6$-alkyl group. Most preferably, $R_1$ and $R_2$ both represent a hydrogen atom.

In the middle part of the organic silicon compound (a1), there is the structural unit or linker -L- which stands for a linear or branched divalent $C_1$-$C_{20}$-alkylene group.

Preferably, -L- represents a linear divalent $C_1$-$C_{20}$-alkylene group. Further preferably, -L- represents a linear divalent $C_1$-$C_6$-alkylene group. Particularly preferably, -L- stands for a methylene group (—$CH_2$—), an ethylene group (—$CH_2$—$CH_2$—), a propylene group (—$CH_2$—$CH_2$—$CH_2$—) or a butylene group (—$CH_2$—$CH_2$—$CH_2$—$CH_2$—). Very preferably, L represents a propylene group (—$CH_2$—$CH_2$—$CH_2$—).

The organic silicon compounds (a1) of the formula (I)

$$R_1R_2N\text{-}L\text{-}Si(OR_3)_a(R_4)_b \qquad (I),$$

each carry at one end the silicon-comprising grouping —$Si(OR_3)_a(R_4)_b$.

In the terminal structural unit —$Si(OR_3)_a(R_4)_b$ the residue $R_3$ is a hydrogen atom or a $C_1C_6$-alkyl group, and the group R4 is a $C_1$-$C_6$-alkyl group. Particularly preferred are $R_3$ and R4 independently of one another represent a methyl group or an ethyl group.

Here, a represents an integer from 1 to 3, and b represents the integer 3–a. If a stands for the number 3, then b is 0. If a stands for the number 2, then b is equal to 1. If a stands for the number 1, then b is equal to 2.

Dyeings with the best wash fastness could be obtained when the agent (a) comprises at least one organic silicon compound (a1) of formula (I) in which the radicals R3, R4 independently of one another represent a methyl group or an ethyl group.

Furthermore, dyeings with the best wash fastnesses could be obtained if the agent (a) comprises at least one organic silicon compound (a1) corresponding to formula (I): in which the radical a is the number 3. In this case, the radical b stands for the number 0.

In a further preferred embodiment, an agent (a) is wherein it comprises at least one organic silicon compound (a1) of formula (I), wherein $R_3$, R4 independently of one another represent a methyl group or an ethyl group, and
a stands for the number 3 and
b stands for the number 0.

In a further preferred embodiment, the method is wherein the agent (a) comprises at least one organic silicon compound (a1) of formula (I), $R_1R_2N\text{-}L\text{-}Si(OR_3)_a(R_4)_b$      (I), where
$R_1$, $R_2$ both represent a hydrogen atom, and
L for a linear, two-valued $C_1$-$C_6$-alkylene group, preferably for a propylene group ($-CH_2-CH_2-CH_2-$) or for an ethylene group ($-CH_2-CH_2-$), is present,
$R_3$ represents a hydrogen atom, an ethyl group or a methyl group,
R4 is a methyl group or an ethyl group,
a stands for the number 3 and
b stands for the number 0.

If b stands for the number 0, the radical R4 does not occur in the compounds of the formula (I).

Accordingly, in a further preferred embodiment, the method is wherein the agent (a) comprises at least one organic silicon compound (a1) of formula (I), $R_1R_2N\text{-}L\text{-}Si(OR_3)_a(R_4)_b$      (I), where
$R_1$, $R_2$ both represent a hydrogen atom, and
L stands for a linear, two-valued $C_1$-$C_6$-alkylene group, preferably for a propylene group ($-CH_2-CH_2-CH_2-$) or for an ethylene group ($-CH_2-CH_2-$), is present,
$R_3$ represents a hydrogen atom, an ethyl group or a methyl group,
a stands for the number 3 and
b stands for the number 0.

Organic silicon compounds (a1) of the formula (I) which are particularly suitable for solving the problem are
(3-Aminopropyl)triethoxysilane

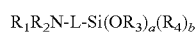

(3-Aminopropyl)trimethoxysilane

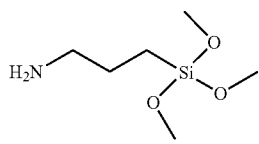

1-(3-aminopropyl)silanetriol

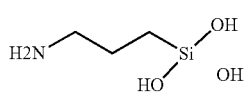

(2-Aminoethyl)triethoxysilane

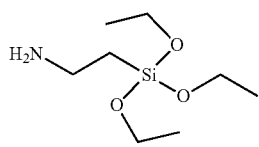

(2-Aminoethyl)trimethoxysilane

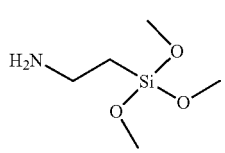

1-(2-aminoethyl)silanetriol

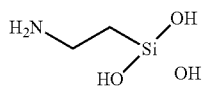

3-Dimethylaminopropyl)trimethoxysilane

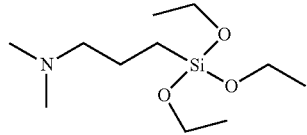 [SMILES: CCO[Si](CCCN(C)C)(OCC)OCC]

1-(3-Dimethylaminopropyl)silanetriol

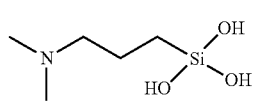

(2-Dimethylaminoethyl)triethoxysilane

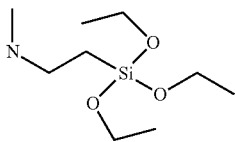

(2-dimethylaminoethyl)trimethoxysilane and/or

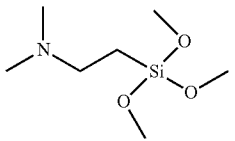

1-(2-dimethylaminoethyl)silanetriol

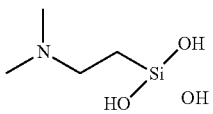

In a further preferred embodiment, the method is wherein the agent (a) comprises at least one organic silicon compound (a1) of formula (I) selected from the group of
(3-Aminopropyl)triethoxysilane
(3-Aminopropyl)trimethoxysilane
1-(3-aminopropyl)silanetriol
(2-Aminoethyl)triethoxysilane
(2-Aminoethyl)trimethoxysilane
1-(2-aminoethyl)silanetriol
(3-Dimethylaminopropyl)triethoxysilane
(3-Dimethylaminopropyl)trimethoxysilane
1-(3-Dimethylaminopropyl)silanetriol
(2-dimethylaminoethyl)triethoxysilane.
(2-dimethylaminoethyl)trimethoxysilane,
1-(2-dimethylaminoethyl)silanetriol
and mixtures thereof.

The above organic silicon compound (a1) of formula (I) is commercially available. (3-Aminopropyl)trimethoxysilane is available for purchase from Sigma-Aldrich, for example. (3-Aminopropyl)triethoxysilane is also commercially available from Sigma-Aldrich.
In a further embodiment, the agent (a) comprises at least one organic silicon compound of formula (II)

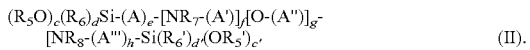

The organosilicon compounds (a1) of the formula (II) each carry at their two ends the silicon-comprising groupings $(R_5O)_c(R_6)_dSi-$ and $-Si(R_6')_{d'}(OR_5')_{c'}$.

In the middle part of the molecule of the formula (II) are the groupings $-(A)_e-$ and $-[NR_7-(A')]_f-$ and $[O-(A'')]_g-$ and $-[NR_8-(A''')]_h-$, where each of the radicals e, f, g and h independently of one another can be the number 0 or 1, with the proviso that at least one of the radicals e, f, g and his other than 0. In other words, an organic silicon compound (a1) of formula (II) comprises at least one grouping selected from the group of -(A)- and $-[NR_7-(A')]-$ and $-[O-(A'')]-$ and $-[NR_8-(A''')]-$.

In the two terminal structural units $(R_5O)_c(R_6)_dSi-$ and $-Si(R_6')_{d'}(OR_5')_{c'}$ the radicals R5, R5', R5'' independently of one another represent a hydrogen atom or a $C_1$-$C_6$ alkyl group. R6, R6' and R6'' independently represent a $C_1$-$C_6$ alkyl group.

Here c stands for an integer from 1 to 3, and d stands for the integer 3−c. If c stands for the number 3, then d is 0. If c stands for the number 2, then d is equal to 1. If c stands for the number 1, then d is equal to 2.

Similarly, c' represents an integer from 1 to 3, and d' represents the integer 3−c'. If c' stands for the number 3, then d' is equal to 0. If c' stands for the number 2, then d' is equal to 1. If c' stands for the number 1, then d' is equal to 2.

Colorings with the best wash fastness could be obtained when the radical c and c' both stand for the number 3. In this case, d and d' both stand for the number 0. In a further preferred embodiment, the method is wherein the agent (a) comprises at least one organic silicon compound (a1) of formula (II),

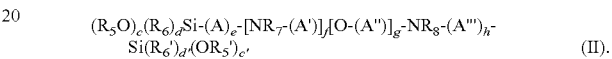

where
R5 and R5' independently represent a methyl group or an ethyl group,
c and c' both stand for the number 3 and
d and d' both stand for the number 0.

When c and c' both represent the number 3 and d and d' both represent the number 0, the organic silicon compounds correspond to the formula (IIa)

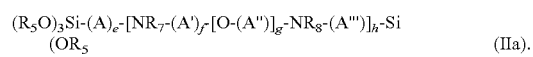

The radicals e, f, g, and h can independently represent the number 0 or 1, with at least one radical from e, f, g, and h being different from zero. The abbreviations e, f, g and h therefore define which of the groupings $-(A)_e-$ and $-[NR_7-(A')]_f-$ and $-[O-(A'')]_g-$ and $-[NR_8-(A''')]_h-$ are in the middle part of the organic silicon compound of formula (II).

In this context, the presence of certain groupings has proven to be particularly beneficial in terms of increasing wash fastness. Particularly good results could be obtained if at least two of the residues e, f, g and h stand for the number 1. Very preferably, e and f both stand for the number 1. Furthermore, g and h both represent the number 0.

When e and f both represent the number 1 and g and h both represent the number 0, the organic silicon compounds (a1) correspond to the formula (IIb)

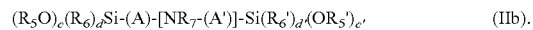

Radicals A, A', A'', A''' and A'''' independently represent a linear or branched divalent $C_1$-C20 alkylene group. Preferably, the radicals A, A', A'', A''' and A'''' independently represent a linear, divalent $C_1$-$C_{20}$-alkylene group. Further preferably, A, A', A'', A''' and A'''' independently represent a linear divalent $C_1$-$C_6$ alkylene group. Particularly preferably, the radicals A, A', A'', A''' and A'''' independently represent a methylene group (—CH2—), an ethylene group (—CH2-CH2-), a propylene group (—CH2-CH2-CH2-) or a butylene group (—CH2-CH2-CH2-CH2-). Very preferably, the radicals A, A', A'', A''' and A'''' represent a propylene group (—CH2-CH2-CH2-).

When the radical f represents the number 1, the organic silicon compound of formula (II) comprises a structural grouping $-[NR_7-(A')]-$.

When the radical h represents the number 1, the organic silicon compound of formula (II) comprises a structural grouping $-[NR_8-(A''')]-$.

Here the residues $R_7$ and $R_8$ independently of one another represent a hydrogen atom, a $C1$-$C_6$-Alkyl group, a hydroxy-$C1$-$C_6$ alkyl group, a $C2$-$C_6$ alkenyl group, an amino-$C1$-$C_6$ alkyl group or a group of the formula (III)

$$-(A'''')-Si(R_6'')_{d''}(OR_5'')_{c''} \quad (III).$$

Very preferably, the radicals $R_7$ and $R_8$ independently of one another represent a hydrogen atom, a methyl group, a 2-hydroxyethyl group, a 2-alkenyl group, a 2-aminoethyl group or a group of the formula (III).

If the radical f represents the number 1 and the radical h represents the number 0, the organic silicon compound (a1) comprises the grouping $[NR_7\text{-}(A')]$, but not the grouping $—[NR_8\text{-}(A''')]$. If the radical R7 now stands for a grouping of the formula (III), the agent (a) comprises an organic silicon compound with 3 reactive silane groups.

In a further preferred embodiment, the method is wherein the agent (a) comprises at least one organic silicon compound (a1) of formula (II), $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (II),$$

where
e and f both stand for the number 1,
g and h both stand for the number 0,
A and A' independently for a linear, two-valued $C_1$-$C_6$-alkylene group, and
R7 represents a hydrogen atom, a methyl group, a 2-hydroxyethyl group, a 2-alkenyl group, a 2-aminoethyl group or a group of formula (III).

In a further preferred embodiment, the method is wherein the agent (a) comprises at least one organic silicon compound (a1) of formula (II), wherein
e and f both stand for the number 1,
g and h both stand for the number 0,
A and A' independently of each other for a methylene group (—CH2-), an ethylene group (—CH2-CH2-) or a propylene group (—CH2-CH2-CH2) are present, and
R7 represents a hydrogen atom, a methyl group, a 2-hydroxyethyl group, a 2-alkenyl group, a 2-aminoethyl group or a group of formula (III).

Organic silicon compounds (a1) of the formula (II) that are well suited for solving the problem are 3-(Trimethoxysilyl)-N-[3-(trimethoxysilyl)propyl]-1-propanamine

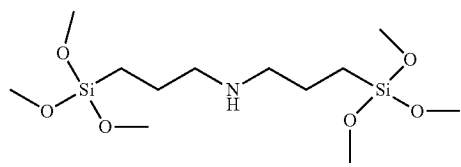

3-(Triethoxysilyl)-N-[3-(triethoxysilyl)propyl]-1-propanamine

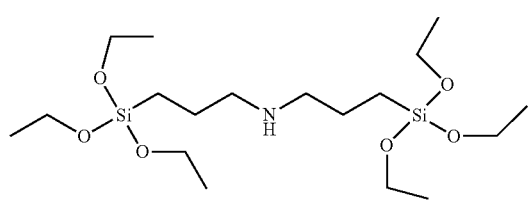 [SMILES: CCO[Si](CCCNCCC[Si](OCC)(OCC)OCC)(OCC)OCC]

N-methyl-3-(trimethoxysilyl)-N-[3-(trimethoxysilyl)propyl]-1-propanamine

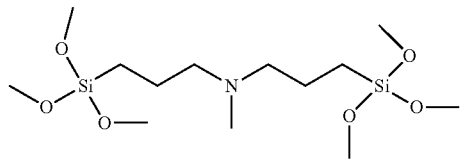

N-methyl-3-(triethoxysilyl)-N-[3-(triethoxysilyl)propyl]-1-propanamine

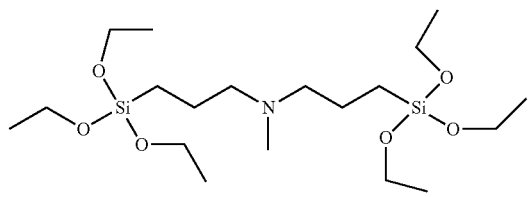 [SMILES: CCO[Si](CCCN(C)CCC[Si](OCC)(OCC)OCC)(OCC)OCC]

2-[Bis[3-(trimethoxysilyl)propyl]amino]ethanol

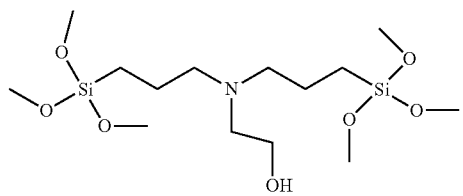

2-[Bis[3-(triethoxysilyl)propyl]amino]ethanol

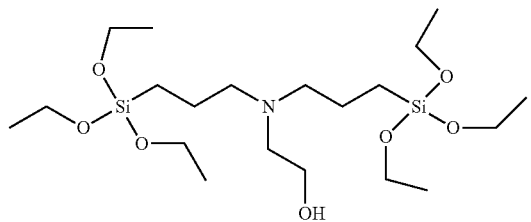 [SMILES: CCO[Si](CCCN(CCO)CCC[Si](OCC)(OCC)OCC)(OCC)OCC]

3-(Trimethoxysilyl)-N,N-bis[3-(trimethoxysilyl)propyl]-1-propanamine

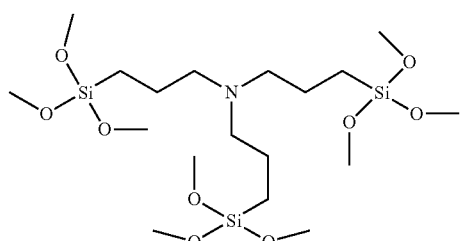

3-(Triethoxysilyl)-N,N-bis[3-(triethoxysilyl)propyl]-1-propanamine

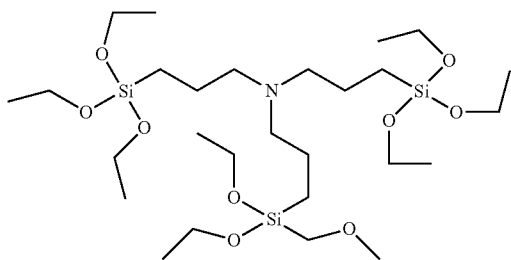 [SMILES: CCO[Si](CCCN(CCC[Si](OCC)(OCC)OCC)CCC[Si](OCC)(OCC)OCC)(COC)OCC]

N1,N1-bis[3-(trimethoxysilyl)propyl]-1,2-ethanediamine,

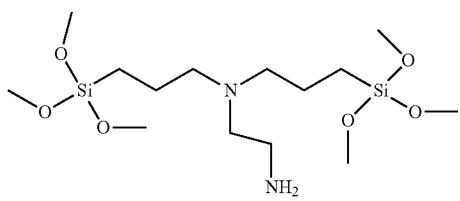

N1,N1-bis[3-(triethoxysilyl)propyl]-1,2-ethanediamine,

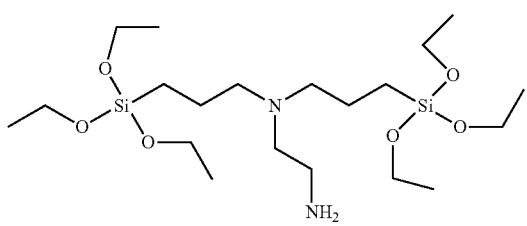 [SMILES: CCO[Si](CCCN(CCN)CCC[Si](OCC)(OCC)OCC)(OCC)OCC]

N,N-bis[3-(trimethoxysilyl)propyl]-2-propen-1-amine

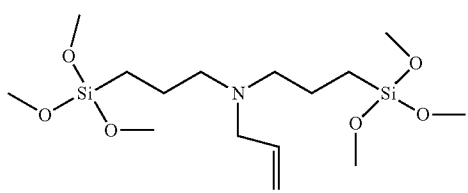

N,N-bis[3-(triethoxysilyl)propyl]-2-propen-1-amine

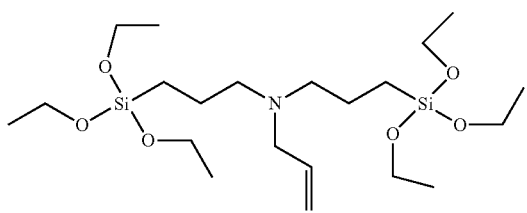 [SMILES: C=CCN(CCC[Si](OCC)(OCC)OCC)CCC[Si](OCC)(OCC)OCC]

The above organic silicon compound (a1) of formula (II) is commercially available. Bis(trimethoxysilylpropyl)amines with CAS number 82985-35-1 can be purchased from Sigma-Aldrich, for example.

Bis[3-(triethoxysilyl)propyl]amines with CAS number 13497-18-2 can be purchased, for example, from Sigma-Aldrich.

N-methyl-3-(trimethoxysilyl)-N-[3-(trimethoxysilyl)propyl]-1-propanamine is alternatively known as bis(3-trimethoxysilylpropyl)-N-methylamine and can be purchased commercially from Sigma-Aldrich or Fluorochem.

3-(Triethoxysilyl)-N,N-bis[3-(triethoxysilyl)propyl]-1-propanamine with CAS number 18784-74-2 can be purchased, for example, from Fluorochem or Sigma-Aldrich.

In a further preferred embodiment, an agent (a) is wherein it comprises at least one organic silicon compound (a1) of formula (II) selected from the group of
3-(Trimethoxysilyl)-N-[3-(trimethoxysilyl)propyl]-1-propanamine
3-(Triethoxysilyl)-N-[3-(triethoxysilyl)propyl]-1-propanamine
N-methyl-3-(trimethoxysilyl)-N-[3-(trimethoxysilyl)propyl]-1-propanamine
N-methyl-3-(triethoxysilyl)-N-[3-(triethoxysilyl)propyl]-1-propanamine
2-[Bis[3-(trimethoxysilyl)propyl]amino]-ethanol
2-[Bis[3-(triethoxysilyl)propyl]amino]-ethanol
3-(trimethoxysilyl)-N,N-bis[3-(trimethoxysilyl)propyl]-1-propanamine
3-(triethoxysilyl)-N,N-bis[3-(triethoxysilyl)propyl]-1-propanamine
N1,N1-bis[3-(trimethoxysilyl)propyl]-1,2-ethanediamine,
N1,N1-bis[3-(triethoxysilyl)propyl]-1,2-ethanediamine,
N,N-bis[3-(trimethoxysilyl)propyl]-2-propen-1-amine and/or
N,N-bis[3-(triethoxysilyl)propyl]-2-propen-1-amine.

In further dyeing tests, it has also been found to be particularly advantageous if the agent (a) applied to the keratinous material in the process comprises at least one organic silicon compound (a1) of the formula (IV)

$$R_9Si(OR_{10})_k(R_{11})_m \qquad (IV).$$

The organic silicon compound(s) (a1) of formula (IV) may also be referred to as silanes of the alkylalkoxysilane or alkylhydroxysilane type, $$R_9Si(OR_{10})_k(R_{11})_m \qquad (IV),$$

where
$R_9$ represents a $C_1$-$C_{18}$-alkyl group,
$R_{10}$ represents a hydrogen atom or a $C_1$-$C_6$-alkyl group,
$R_{11}$ represents a $C_1$-$C_6$-alkyl group
k is an integer from 1 to 3, and
m stands for the integer 3−k.

In a further preferred embodiment, the method is wherein the agent (a) comprises at least one organic silicon compound (a1) of formula (IV).

$$R_9Si(OR_{10})_k(R_{11})_m \qquad (IV),$$

where
$R_9$ is a $C_1$-$C_{18}$-alkyl group,
$R_{10}$ represents a hydrogen atom or a $C_1$-$C_6$-alkyl group,
$R_{11}$ represents a $C_1$-$C_6$-alkyl group
k is an integer from 1 to 3, and
m stands for the integer 3−k.

In a further preferred embodiment, the process is wherein the agent (a) comprises, in addition to the organic silicon compound or compounds (a1) of the formula (I), at least one further organic silicon compound (a1) of the formula (IV)

$$R_9Si(OR_{10})_k(R_{11})_m \qquad (IV),$$

where
R$_9$ is a C$_1$-C$_{18}$-alkyl group,
R$_{10}$ represents a hydrogen atom or a C$_1$-C$_6$-alkyl group,
R11 represents a C$_1$-C$_6$-alkyl group
k is an integer from 1 to 3, and
m stands for the integer 3–k.

In a further preferred embodiment, the method is wherein the agent (a) comprises, in addition to the organic silicon compound or compounds (a1) of the formula (II), at least one further organic silicon compound (a1) of the formula (IV)

$$R_9Si(OR_{10})_k(R_{11})_m \quad (IV),$$

where
R$_9$ is a C$_1$-C$_{18}$-alkyl group,
R$_{10}$ represents a hydrogen atom or a C$_1$-C$_6$-alkyl group,
R11 represents a C$_1$-C$_6$-alkyl group
k is an integer from 1 to 3, and
m stands for the integer 3–k.

In a further preferred embodiment, the process is wherein the agent (a) comprises, in addition to the organic silicon compound or compounds (a1) of the formula (I) and/or (II), at least one further organic silicon compound (a1) of the formula (IV)

$$R_9Si(OR_{10})_k(R_{11})_m \quad (IV),$$

where
R$_9$ is a C$_1$-C$_6$-alkyl group,
R$_{10}$ represents a hydrogen atom or a C$_1$-C$_6$-alkyl group,
R$_{11}$ represents a C$_1$-C$_6$-alkyl group
k is an integer from 1 to 3, and
m stands for the integer 3–k.

In the organic silicon compounds (a1) of the formula (IV), the radical R$_9$ represents a C1-C1$_8$-alkyl group. This C1-C1$_8$-alkyl group is saturated and can be linear or branched. Preferred stands R$_9$ is a linear C1-C1$_8$-alkyl group. Preferred stands R$_9$ represents a methyl group, an ethyl group, an n-propyl group, an n-butyl group, an n-pentyl group, an n-hexyl group, an n-octyl group, an n-dodecyl group or an n-octadecyl group. Particularly preferred is R$_9$ is a methyl group, an ethyl group, a propyl group, an n-hexyl group or an n-octyl group. In the organic silicon compounds (a1) of the formula (IV), the radical R10 is a hydrogen atom or a C1-C$_6$-alkyl group. Particularly preferred is R10 is a methyl group or an ethyl group. In the organic silicon compounds (a1) of the form (IV), the radical R11 represents a C1-C$_6$-alkyl group. Particularly preferably, R11 represents a methyl group or an ethyl group.

Furthermore, k stands for an integer from 1 to 3, and m stands for the integer 3–k. If k stands for the number 3, then m is equal to 0. If k stands for the number 2, then m is equal to 1. If k stands for the number 1, then m is equal to 2.

Dyeings with the best wash fastness were obtained when an agent (a) comprising at least one organic silicon compound (a1) corresponding to formula (IV): in which the radical k is the number 3, was used in the process. In this case, the radical m stands for the number 0.

Organic silicon compounds (a1) of the formula (IV) which are particularly suitable for solving the problem as contemplated herein are
Methyltrimethoxysilane

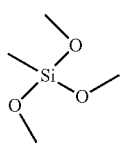

Methyltriethoxysilane

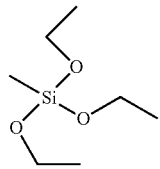

Ethyltrimethoxysilane

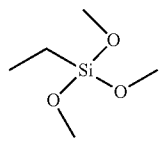

Ethyltriethoxysilane

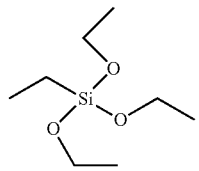

n-Hexyltrimethoxysilane

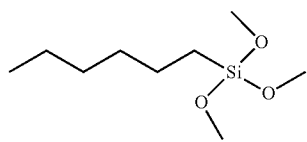

n-Hexyltriethoxysilane

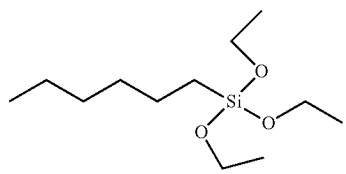 [SMILES: CCCCCC[Si](OCC)(OCC)OCC]

n-Octyltrimethoxysilane

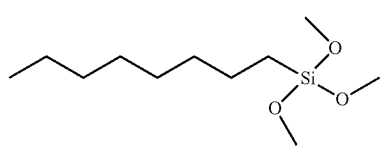

n-Octyltriethoxysilane

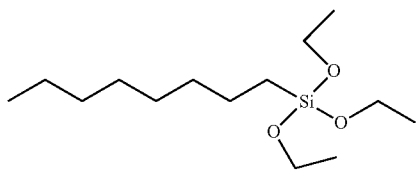 [SMILES: CCCCCCCC[Si](OCC)(OCC)OCC]

n-Dodecyltrimethoxysilane and/or

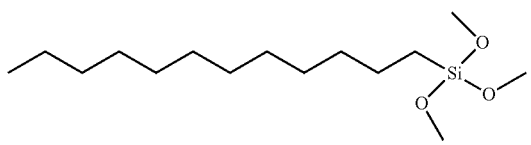 [SMILES: CCCCCCCCCCCC[Si](OC)(OC)OC]

n-Dodecyltriethoxysilane.

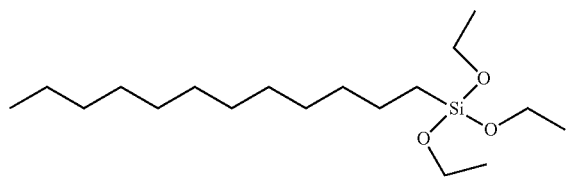 [SMILES: CCCCCCCCCCCC[Si](OCC)(OCC)OCC]

In a further preferred embodiment, the method is wherein the agent (a) comprises at least one organic silicon compound (a1) of formula (IV) selected from the group of
Methyltrimethoxysilane
Methyltriethoxysilane
Ethyltrimethoxysilane
Ethyltriethoxysilane
Propyltrimethoxysilane
Propyltriethoxysilane
Hexyltrimethoxysilane
Hexyltriethoxysilane
Octyltrimethoxysilane
Octyltriethoxysilane
Dodecyltrimethoxysilane
Dodecyltriethoxysilane
Octadecyltrimethoxysilane and/or
Octadecyltriethoxysilane.

In the course of the work leading to this present disclosure, it was found that particularly stable and uniform films could be obtained on the keratinous material even when the agent (a) included two organic silicon compounds that were structurally different from each other.

In a further preferred embodiment, a method is wherein the agent (a) comprises at least two structurally different organic silicon compounds.

In a preferred embodiment, a process is wherein an agent (a) comprising at least one organic silicon compound of formula (I) and at least one organic silicon compound of formula (IV) is applied to the keratinous material.

In an explicitly quite particularly preferred embodiment, the process is wherein an agent (a) is applied to the keratinous material, which agent (a1) comprises at least one organic silicon compound of the formula (I) selected from the group of (3-aminopropyl)triethoxysilane and (3-aminopropyl)trimethoxysilane and additionally comprises at least one organic silicon compound of formula (IV) selected from the group of methyltrimethoxysilane, methyltriethoxysilane, ethyltrimethoxysilane, ethyltriethoxysilane, propyltrimethoxysilane, propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane and octadecyltriethoxysilane.

The organic silicon compounds described above are reactive compounds. In this context, it has been found preferable if the agent (a)—based on the total weight of the agent (a)—comprises one or more organic silicon compounds (a1) in a total amount of 0.1 to 20% by weight, preferably 0.5 to 15% by weight and particularly preferably 5.0 to 10% by weight.

In this context, it has been found to be particularly preferred if the agent (a) comprises—based on the total weight of the agent (a)—one or more organic silicon compounds (a1) of the formula (I) and/or (II) in a total amount of 0.1 to 20% by weight, preferably 0.2 to 15% by weight and particularly preferably 0.2 to 3% by weight.

It has further been found to be particularly preferred if the agent (a) comprises—based on the total weight of the agent (a)—one or more organic silicon compounds (a1) of the formula (IV) in a total amount of 0.1 to 20% by weight, preferably 0.5 to 15% by weight and particularly preferably 2 to 8% by weight.

Even the addition of small amounts of water leads to hydrolysis in organic silicon compounds with at least one hydrolysable group. The hydrolysis products and/or organic silicon compounds having at least one hydroxy group may react with each other in a condensation reaction. For this reason, both the organosilicon compounds having at least one hydrolysable group and their hydrolysis and/or condensation products may be present in the agent (a). When organosilicon compounds having at least one hydroxyl group are used, both the organic silicon compounds having at least one hydroxyl group and their condensation products may be present in the agent (a).

A condensation product is understood to be a product formed by the reaction of at least two organic silicon compounds each having at least one hydroxyl group or hydrolysable group per molecule with elimination of water and/or with elimination of an alkanol. The condensation products can be, for example, dimers, but also trimers or oligomers, with the condensation products being in equilibrium with the monomers. Depending on the amount of water used or consumed in the hydrolysis, the equilibrium shifts from monomeric organic silicon compounds to condensation product.

Particularly good results were obtained when organic silicon compounds (a1) of formula (I) and/or (II) were used in the process. Since, as already described above, hydrolysis/condensation already starts at traces of moisture, the hydrolysis and/or condensation products of the organic silicon compounds (I) and/or (II) are also included in this embodiment.

Particularly resistant strains could be obtained when using an alkaline adjusted agent (a). Preferably, agent (a) comprises water and has a pH of from 7 to 11.5, preferably from 7.5 to 11, and more preferably from 8 to 10.5.

In a further very particularly preferred embodiment, the process is wherein the agent (a) has a pH of from 7 to 11.5, preferably from 7.5 to 11 and particularly preferably from 8 to 10.5.

Agent (b)

The agent (b) is exemplified by the presence of at least one color-imparting compound (b1) and at least one film-forming polymer (b2). The colorant compound (b1) comprises at least one effect pigment comprising a) a substrate platelet comprising synthetic mica, and ß) a coating comprising at least a first metal oxide (hydrate) layer.

The effect pigment has a substrate platelet comprising synthetic mica.

Synthetic mica is also known as synthetic fluorophlogopite (INCI: Synthetic Fluorophlogopite) and is preferably a fluorophlogopite of the empirical formula $KMg_3(AlSi_3)O_{10}F_2$, $KMg_2^{1/2}(Si_4O_{10})F_2$ or $NaMg_2^{1/2}(Si_4O_{10})F_2$, in preferably a fluorophlogopite of the empirical formula $KMg_3(AlSi_3)O_{10}F_2$.

In contrast to synthetically produced mica particles, natural mica particles have the disadvantage that they may contain impurities due to incorporated foreign ions. These impurities can change the color tone and/or reduce the brightness L*. Typical impurities of, for example, natural mica include nickel, chromium, copper, iron, manganese, lead, cadmium, arsenic and/or antimony and/or their compounds, which can give the natural mica a color. The production of a synthetic mica can be controlled in a targeted manner so that the resulting synthetic mica particles have as few defects as possible. Furthermore, particle size can also be controlled and managed in the production of a synthetic mica. In addition, synthetically produced mica particles have a smooth, uniform surface that leads to more uniform deposition of materials such as metal oxide (hydrate)s, resulting in high color purity and reliability.

One advantage over effect pigments based on metal substrate platelets, in particular aluminum substrate platelets, is that synthetically produced mica particles are corrosion-resistant, especially when in contact with water.

The substrate platelet preferably has an average thickness of 50 to 1500 nm and more preferably 90 to 1000 nm.

The size of the substrate platelet can be tailored to the specific application, for example the desired effect on a keratinous material. Typically, the substrate platelets have an average largest diameter of about 1 to 200 µm, particularly about 5 to 100 µm, and even more preferably about 5 to 25 µm.

The substrate platelets can have different shapes. For example, lamellar or lenticular substrate platelets can be used as substrate platelets. Lamellar substrate platelets are exemplified by an irregularly structured edge and are also referred to as "cornflakes" due to their appearance. Lenticular substrate plaquettes have an essentially regular round edge and are also known as "silver dollars" because of their appearance.

A coating can change the surface properties and/or optical properties of the effect pigment and increase the mechanical and chemical load-bearing capacity of the effect pigments. For example, only the upper and/or lower side of the substrate wafer may be coated, with the side surfaces being recessed. Preferably, the entire surface of the substrate platelets, including the side surfaces, is covered with the coating. The substrate platelets are preferably completely encased by the coating.

The coating may include one or more metal oxide (hydrate) layers. In a preferred embodiment, the coating has only a first layer. In a likewise preferred embodiment, the coating has a total of at least two, preferably two or three, layers. It may be preferred to have the coating form a first metal oxide (hydrate) layer A and a second metal oxide (hydrate) layer B, said second metal oxide (hydrate) layer B being different from said first metal oxide (hydrate) layer A. Preferably, the first metal oxide (hydrate) layer A is located between the second metal oxide (hydrate) layer B and the surface of the substrate wafer. It may be preferred that the coating has three layers A, B and C. In this embodiment, between the second metal oxide (hydrate) layer B and the surface of the substrate wafer is the first metal oxide (hydrate) layer A, and on the second metal oxide (hydrate) layer B is a third layer C that is different from the underlying second layer B.

It is quite preferred that the coating comprises a first metal oxide (hydrate) layer and a second metal oxide (hydrate) layer.

Suitable materials for the at least one first metal oxide (hydrate) layer are any metal oxides or metal oxide hydrates that can be permanently applied to the substrate platelets, comprising synthetic mica. The materials should preferably be film-applicable.

In a preferred embodiment, the first metal oxide (hydrate) layer comprises a metal oxide (hydrate) selected from the group of titanium dioxide ($TiO_2$), iron oxide ($Fe_2O_3$ and/or $Fe_3O_4$), and mixtures thereof. In a very preferred embodiment, the first metal oxide (hydrate) layer comprises titanium dioxide ($TiO_2$) and/or iron oxide ($Fe_2O_3$). In a highly preferred embodiment, the first metal oxide (hydrate) layer comprises titanium dioxide ($TiO_2$). Preferably, the entire surface of the substrate platelets, including the side surfaces, is coated by the at least one first metal oxide (hydrate) layer.

The at least one first metal oxide (hydrate) layer can be prepared, for example, wet-chemically using a metal alkoxide, titanium alkoxide such as titanium tetraethylate (tetraethyl orthotitanate) or titanium tetraisopropanolate (tetraisopropyl orthotitanate).

Alternatively, the at least one first metal oxide (hydrate) layer can be produced, for example, by hydrolytic decomposition of one or more organic metal compounds and/or by precipitation of one or more dissolved metal salts, as well as any subsequent post-treatment (for example, transferring a formed hydroxide-comprising layer to the oxide layers by annealing).

The second metal oxide (hydrate) layer, if present, is different from the first metal oxide (hydrate) layer.

Metal oxides (hydrates) suitable for the second metal oxide (hydrate) layer are tin oxide ($SnO_2$), silicon oxide ($SiO_2$), aluminum oxide (Al2O3) and/or iron oxide ($Fe_2O_3$ and/or $Fe_3O_4$). Accordingly, it is preferred that the second metal oxide (hydrate) layer is a metal oxide (hydrate) selected from the group of tin oxide ($SnO_2$), silicon oxide ($SiO_2$), aluminum oxide (Al2O3), Iron oxide ($Fe_2O_3$ and/or $Fe_3O_4$) and mixtures thereof. It is particularly preferred that the second metal oxide (hydrate) layer is tin oxide ($SnO_2$) is present.

The second metal oxide (hydrate) layer may further comprise a selectively absorbing dye or pigment. Suitable dyes and/or pigments include, for example, carmine, ferric (III)hexacyanidoferrate(II/III), and chromium oxide green ($Cr_2O_3$).

The effect pigments may have a further layer C, which acts as a protective layer and comprises a metal oxide (hydrate) or a polymer, for example a synthetic resin. Suitable metal oxide (hydrates)s includes silicon (di)oxide, silicon oxide hydrate, aluminum oxide, aluminum oxide hydrate, zinc oxide, tin oxide, titanium dioxide, zirconium oxide, iron(III)oxide, and chromium(III)oxide. Preferred is silicon dioxide.

It is particularly preferred that the effect pigment is a substrate platelet of synthetic mica (INCI: Synthetic Fluorophlogopite) and a first metal oxide (hydrate) layer comprising titanium dioxide ($TiO_2$).

It is also preferred that the effect pigment is a substrate platelet of synthetic mica (INCI: Synthetic Fluorophlogopite) and a first metal oxide (hydrate) layer comprising iron(III)oxide($Fe_2O_3$).

It is also preferred that the effect pigment is a substrate platelet of synthetic mica (INCI: Synthetic Fluorophlogopite), a first metal oxide (hydrate) layer comprising titanium dioxide ($TiO_2$) and iron(III)oxide ($Fe_2O_3$), and a second metal oxide (hydrate) layer comprising tin dioxide ($SnO_2$).

It is highly preferred that the effect pigment is a substrate platelet of synthetic mica (INCI: Synthetic Fluorophlogopite), a first metal oxide (hydrate) layer comprising titanium dioxide ($TiO_2$), and a second metal oxide (hydrate) layer comprising tin dioxide ($SnO_2$).

Typically, the effect pigments have an average largest diameter of about 1 to 200 μm, particularly about 5 to 100 μm and even more preferably about 5 to 25 μm.

Preferably, the effect pigments have an average particle size $D_{50}$ of 3 to 150 μm, preferably of 5 to 45 μm and particularly preferably of 10 to 30 μm.

Very particularly preferred effect pigments have a substrate platelet of synthetic mica (INCI: Synthetic Fluorophlogopite), a first metal oxide (hydrate) layer comprising titanium dioxide ($TiO_2$), a second metal oxide (hydrate) layer comprising tin dioxide (SnO2), and a mean particle size D50 of 10 to 14 μm.

Effect pigments comprising α) a substrate platelet comprising synthetic mica, and ß) a coating comprising at least a first metal oxide (hydrate) layer are available, for example, under the name Timiron® from the Merck company or under the name SYNCRYSTAL from the Eckart company.

The adhesion and abrasion resistance of effect pigments comprising α) a substrate platelet comprising synthetic mica, and ß) a coating comprising at least a first metal oxide (hydrate) layer, in the keratinous material can be further increased by additionally modifying the outermost layer with organic compounds such as silanes, phosphoric acid esters, titanates, borates or carboxylic acids. In this process, the organic compounds are bound to the surface of the outermost, preferably metal oxide-comprising, layer. The outermost layer denotes the layer that is spatially farthest from the substrate platelet. The organic compounds are preferably functional silane compounds that can bind to the outermost layer, which preferably comprises metal oxide. These can be either mono- or bifunctional compounds. Examples of bifunctional organic compounds include methacryloxypropenyltrimethoxysilane, 3-methacryloxypropyltrimethoxysilane, 3-acryloxypropyltrimethoxysilane, 2-acryloxyethyltrimethoxysilane, 3-methacryloxypropyltriethoxysilane, 3-acryloxypropyltrimethoxysilane, 2-methacryloxyethyltriethoxysilane, 2-acryloxyethyltriethoxysilane, 3-methacryloxypropyltris(methoxyethoxy)silane, 3-methacryloxypropyltris(butoxyethoxy)silane, 3-methacryloxy-propyltris(propoxy)silane, 3-methacryloxypropyltris(butoxy)silane, 3-acryloxy-propyltris(methoxyethoxy)silane, 3-acryloxypropyltris(butoxyethoxy)silane, 3-acryl-oxypropyltris(butoxy)silane, vinyltrimethoxysilane, Vinyltriethoxysilane, vinylethyl-dichlorosilane, vinylmethyldiacetoxysilane, vinylmethyldichlorosilane, vinylmethyldiethoxysilane, vinyltriacetoxysilane, vinyltrichlorosilane, phenylvinyldiethoxysilane, or phenylallyldichlorosilane. Furthermore, a modification with a monofunctional silane, an alkylsilane or arylsilane, can be carried out. This has only one functional group that can covalently bond to the surface of the effect pigment comprising α) a substrate platelet comprising synthetic mica, and ß) a coating comprising at least a first metal oxide (hydrate) layer, or, if not completely covered, to the mica surface. The hydrocarbon residue of the silane points away from the pigment. Depending on the type and nature of the hydrocarbon residue of the silane, a different degree of hydrophobicity of the pigment is achieved. Examples of such silanes are hexadecyltrimethoxysilane, propyltrimethoxysilane, etc. Particularly preferably, the effect pigments are surface-modified with a monofunctional silane. Octyltrimethoxysilane, octyltriethoxysilane, hecadecyltrimethoxysilane and hecadecyltriethoxysilane are particularly preferred. Due to the changed surface properties/hydrophobization, an improvement can be achieved in terms of adhesion, abrasion resistance and alignment in the application.

It has been shown that effect pigments with such a coating exhibit even better compatibility with the film formed by agent (a).

Particularly good results could be obtained if the agent (b)—based on the total weight of the agent (b)—comprises one or more effect pigments in a total amount of 0.01 to 10% by weight, preferably 0.1 to 8% by weight, more preferably 0.2 to 6% by weight and very particularly preferably 0.5 to 4.5% by weight.

In addition to the effect pigment, the agent (b) may comprise further colorant compounds selected from the group of pigments and/or direct dyes.

The agent (b) is further wherein it comprises at least one film-forming polymer (b2).

Polymers are understood to be macromolecules with a molecular weight of at least 1000 g/mol, preferably of at least 2500 g/mol, particularly preferably of at least 5000 g/mol, which include identical, repeating organic units. The polymers of the present disclosure may be synthetically produced polymers prepared by polymerizing one type of monomer or by polymerizing different types of monomers that are structurally different from each other. If the polymer is produced by polymerization of a monomer type, it is referred to as homo-polymers. If structurally different monomer types are used in the polymerization, the resulting polymer is called a copolymer.

The maximum molecular weight of the polymer depends on the degree of polymerization (number of polymerized monomers) and the batch size and is partly determined by the polymerization method. In terms of the present disclosure, it is preferred if the maximum molecular weight of the film-forming polymer (b) is not more than $10^7$ g/mol, preferably not more than $10^6$ g/mol, and particularly preferably not more than $10^5$ g/mol.

For the purposes of the present disclosure, a film-forming polymer is understood to be a polymer capable of forming a film on a substrate, for example on a keratinous material or a keratinous fiber. The formation of a film can be demonstrated, for example, by viewing the polymer-treated keratinous material under a microscope.

The film-forming polymers (b2) in the agent (b) can be hydrophilic or hydrophobic. In a first embodiment, it may be preferred to use at least one hydrophobic film-forming polymer in agent (b).

A hydrophobic polymer is defined as a polymer that has a solubility in water at 25° C. (760 mmHg) of less than 1% by weight.

For example, the water solubility of the film-forming hydrophobic polymer can be determined in the following way. 1 g of the polymer is placed in a beaker. Make up to 100 g with water. A stirring fish is added, and the mixture is heated to 25° C. on a magnetic stirrer with stirring. It is stirred for 60 minutes. The aqueous mixture is then visually assessed. If the polymer-water mixture cannot be visually assessed due to high turbidity of the mixture, the mixture is filtered. If a portion of undissolved polymer remains on the filter paper, then the solubility of the polymer is less than 1% by weight.

In particular, the polymers of the acrylic acid type, the polyurethanes, the polyesters, the polyamides, the polyureas, the cellulose polymers, the nitro-cellulose polymers, the silicone polymers, the polymers of the acrylamide type and the polyisoprenes can be mentioned here. Particularly suitable film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred embodiment, a composition (b) is wherein it comprises at least one film-forming hydrophobic polymer (b2) selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming hydrophobic polymers selected from the group of synthetic polymers, polymers obtainable by free-radical polymerization or natural polymers have proved particularly suitable for solving the problem as contemplated herein.

Other particularly well-suited film-forming hydrophobic polymers can be selected from the homopolymers or copolymers of olefins, such as cycloolefins, butadiene, isoprene or styrene, vinyl ethers, vinyl amides, the esters or amides of (meth)acrylic acid with at least one $C_1$-$C_{20}$-alkyl group, an aryl group or a $C_2$-$C_{10}$-hydroxyalkyl group.

Other film-forming hydrophobic polymers may be selected from the homo- or copolymers of isooctyl (meth)acrylate, isononyl (meth)acrylate, 2-ethylhexyl (meth)acrylate, lauryl (meth)acrylate), isopentyl (meth)acrylate, n-butyl (meth)acrylate), isobutyl (meth)acrylate, ethyl (meth)acrylate, methyl (meth)acrylate, tert-butyl (meth)acrylate, stearyl (meth)acrylate, hydroxyethyl (meth)acrylate, 2-hydroxypropyl (meth)acrylate, 3-hydroxypropyl (meth)acrylate and/or mixtures thereof.

Further film-forming hydrophobic polymers can be selected from the homo- or copolymers of (meth)acrylamide, N-alkyl(meth)acrylamides, in those with C2-C18 alkyl groups, such as N-ethyl acrylamide, N-tert-butylacrylamide, le N-octylacrylamide, N-di(C1-C4)alkyl(meth)acrylamide.

Other preferred anionic copolymers are, for example, copolymers of acrylic acid, methacrylic acid or their $C_1$-$C_6$-alkyl esters, as sold under the INCI declaration Acrylates Copolymers. A suitable commercial product is, for example, Aculyn® 33 from Rohm & Haas. However, copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are acrylic acid, methacrylic acid and itaconic acid; suitable alkoxylated fatty alcohols are steareth-20 or ceteth-20.

Very particularly preferred polymers on the market are, for example, Aculyn® 22 (Acrylates/Steareth-20 Methacrylate Copolymer), Aculyn® 28 (Acrylates/Beheneth-25 Methacrylate Copolymer), Structure 2001© (Acryla-tes/Steareth-20 Itaconate Copolymer), Structure 3001® (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez20, Ultrez 21 (Acrylates/C10-30 Alkyl Acrylate Crosspolymer), Synthalen W 2000® (Acrylates/Palmeth-25 Acrylate Copolymer) or the Rohme and Haas distributed Soltex OPT (Acrylates/C12-22 Alkyl methacrylate Copolymer).

Suitable polymers based on vinyl monomers include, for example, the homopolymers and copolymers of N-vinylpyrrolidone, vinylcaprolactam, vinyl-(C1-C6)alkyl-pyrrole, vinyl oxazole, vinyl thiazole, vinyl pyrimidine or vinyl imidazole.

Also particularly suitable are the copolymers octylacrylamide/acrylates/butylaminoethyl methacrylate copolymer, such as those sold commercially by NATIONAL STARCH under the trade names AMPHOMER® or LOVOCRYL® 47, or also, the copolymers of acrylates/octylacrylamides marketed under the trade names DERMACRYL® LT and DERMACRYL® 79 by NATIONAL STARCH.

Suitable polymers based on olefins include, for example, the homopolymers and copolymers of ethylene, propylene, butene, isoprene and butadiene.

In a further embodiment, the film-forming hydrophobic polymers may be the block copolymers comprising at least one block of styrene or the derivatives of styrene. These block copolymers may be copolymers comprising one or more blocks in addition to a styrene block, such as styrene/ethylene, styrene/ethylene/butylene, styrene/butylene, styrene/isoprene, styrene/butadiene. Corresponding polymers are sold commercially by BASF under the trade name "Luvitol HSB".

Surprisingly, it was found that particularly intense and wash fastness colorations could be obtained when agent (b) included at least one film-forming polymer (b2) selected from the group of acrylic acid homopolymers and copolymers, methacrylic acid homopolymers and copolymers, acrylic acid ester homopolymers and copolymers, methacrylic acid ester homopolymers and copolymers, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further preferred embodiment, a process is wherein the agent (b) comprises at least one film-forming polymer (b2) selected from the group of homopolymers and copolymers of acrylic acid, homopolymers and copolymers of methacrylic acid, homopolymers and copolymers of acrylic acid esters, homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further embodiment, it may be preferred to use at least one hydrophilic film-forming polymer (b2) in the agent (b).

By a hydrophilic polymer is meant a polymer that has a solubility in water at 25° C. (760 mmHg) of more than 1% by weight, preferably more than 2% by weight.

The water solubility of the film-forming hydrophilic polymer can be determined, for example, in the following way. 1 g of the polymer is placed in a beaker. Make up to 100 g with water. A stirring fish is added, and the mixture is heated to 25° C. on a magnetic stirrer with stirring. It is stirred for 60 minutes. The aqueous mixture is then visually assessed. A completely dissolved polymer appears macroscopically homogeneous. If the polymer-water mixture cannot be visually assessed due to high turbidity of the mixture, the mixture is filtered. If no undissolved polymer remains on the filter paper, then the solubility of the polymer is greater than 1% by weight.

Nonionic, anionic and cationic polymers can be used as film-forming, hydrophilic polymers.

Suitable film-forming hydrophilic polymers may be selected, for example, from the group comprising polyvinylpyrrolidone (co)polymers, polyvinyl alcohol (co)polymers, vinyl acetate (co)polymers, the carboxyvinyl (co) polymers, the acrylic acid (co)polymers, the methacrylic acid (co)polymers, the natural gums, the polysaccharides and/or the acrylamide (co)polymers.

Furthermore, it is particularly preferred to use polyvinylpyrrolidone (PVP) and/or a vinylpyrrolidone-comprising copolymer as the film-forming hydrophilic polymer.

In another very particularly preferred embodiment, an agent (b) is wherein it comprises at least one film-forming hydrophilic polymer selected from the group of polyvinylpyrrolidone (PVP) and the copolymers of polyvinylpyrrolidone.

It is further preferred if the agent comprises polyvinylpyrrolidone (PVP) as the film-forming hydrophilic polymer. Surprisingly, the wash fastness of the dyes obtained with PVP-comprising agents (b9 was also very good.

Particularly well-suited polyvinylpyrrolidones are available, for example, under the name Luviskol® K from BASF SE, especially Luviskol® K 90 or Luviskol® K 85 from BASF SE.

Another explicitly very suitable polyvinylpyrrolidone (PVP) can be the polymer PVP K30, which is sold by the company Ashland (ISP, POI Chemical). PVP K 30 is a polyvinylpyrrolidone that is very soluble in cold water and has the CAS number 9003-39-8. The molecular weight of PVP K 30 is about 40000 g/mol.

Other particularly well-suited polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115, which are available from BASF.

The use of film-forming hydrophilic polymers (b2) from the group of copolymers of polyvinylpyrrolidone also led to particularly good and washfast color results.

In this context, vinylpyrrolidone-vinyl ester copolymers, such as those sold under the trademark Luviskol® (BASF), can be mentioned as particularly suitable film-forming, hydrophilic polymers. Luviskol® VA 64 and Luviskol® VA 73, each vinylpyrrolidone/vinyl acetate copolymers, are particularly preferred nonionic polymers.

Of the vinylpyrrolidone-comprising copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are very preferably used in the cosmetic compositions.

Vinylpyrrolidone-vinyl acetate copolymers are marketed by BASF SE under the name Luviskol® VA. For example, a VP/vinyl caprolactam/DMAPA acrylates copolymer is sold under the trade name Aquaflex® SF-40 by Ashland Inc. For example, a VP/DMAPA acrylates copolymer is marketed as Styleze CC-10 by Ashland and is a highly preferred vinylpyrrolidone-comprising copolymer.

Other suitable copolymers of polyvinylpyrrolidone may include those obtained by reacting N-vinylpyrrolidone with at least one further monomer selected from the group of V-vinylformamide, vinyl acetate, ethylene, propylene, acrylamide, vinylcaprolactam, vinylcaprolactone and/or vinyl alcohol.

In another very particularly preferred embodiment, an agent (b) is wherein it comprises at least one film-forming, hydrophilic polymer (b2) selected from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers.

Another suitable copolymer of vinylpyrrolidone is the polymer known under the INCI name maltodextrin/VP copolymer.

Furthermore, intensively colored keratinous material, especially hair, could be obtained with very good wash fastness properties when a nonionic film-forming hydrophilic polymer was used as the film-forming hydrophilic polymer.

In a further embodiment, the agent (b) may comprise at least one nonionic film-forming hydrophilic polymer (b2).

As contemplated herein, a nonionic polymer is a polymer which, in a protic solvent—such as water, for example—does not carry structural units with permanent cationic or anionic groups under standard conditions, which must be compensated by counterions while maintaining electroneutrality. Cationic groups include, for example, quaternized ammonium groups but not protonated amines. Anionic groups include, for example, carboxylic and sulfonic acid groups.

Agents are particularly preferred which contain, as a nonionic, film-forming, hydrophilic polymer, at least one polymer selected from the group of polyvinylpyrrolidone, Copolymers of N-vinylpyrrolidone and vinyl esters of carboxylic acids comprising 2 to 18 carbon atoms of N-vinylpyrrolidone and vinyl acetate, Copolymers of N-vinylpyrrolidone and N-vinylimidazole and methacrylamide, Copolymers of N-vinylpyrrolidone and N-vinylimidazole and acrylamide, Copolymers of N-vinylpyrrolidone with N,N-di(C1 to C4)-alkylamino-(C2 to C4)-alkyl acrylamide.

If copolymers of N-vinylpyrrolidone and vinyl acetate are used, it is again preferred if the molar ratio of the structural units included from the monomer N-vinylpyrrolidone to the structural units of the polymer included from the monomer vinyl acetate is in the range from 20 to 80 to 80 to 20, particularly from 30 to 70 to 60 to 40. Suitable copolymers of vinylpyrrolidone and vinyl acetate are available, for example, under the trademark Luviskol® VA 37, Luviskol® VA 55, Luviskol® VA 64 and Luviskol® VA 73 from BASF SE. Another particularly preferred polymer is selected from polymers with the INCI designation VP/Methacrylamide/

Vinyl Imidazole Copolymer, which are available, for example, under the trade name Luviset Clear from BASF SE.

Another particularly preferred nonionic, film-forming, hydrophilic polymer is a copolymer of N-vinylpyrrolidone and N,N-dimethylaminiopropylmethacrylamide, which is sold, for example, by ISP under the INCI designation VP/DMAPA Acrylates Copolymer, e.g., under the trade name Styleze® CC 10.

A cationic polymer is the copolymer of N-vinylpyrrolidone, N-vinylcaprolactam, N-(3-dimethylaminopropyl) methacrylamide and 3-(methacryloylamino)propyl-lauryl-dimethylammonium chloride (INCI designation: Polyquaternium-69), which is marketed, for example, under the trade name AquaStyle® 300 (28-32% by weight active substance in ethanol-water mixture, molecular weight 350000) by the company ISP.

Other suitable film-forming hydrophilic polymers include
  Vinylpyrrolidone-vinylimidazolium methochloride copolymers as offered under the designations Luviquat® FC 370, FC 550 and the INCI designation polyquaternium-16 as well as FC 905 and HM 552,
  Vinylpyrrolidone-vinylcaprolactam-acrylate terpolymers, such as those offered commercially with acrylic acid esters and acrylic acid amides as the third monomer building block, for example under the name Aquaflex® SF 40.

Polyquaternium-11 is the reaction product of diethyl sulfate with a copolymer of vinylpyrrolidone and dimethylaminoethyl methacrylate. Suitable commercial products are available, for example, under the names Dehyquart® CC 11 and Luviquat® PQ 11 PN from BASF SE or Gafquat 440, Gafquat 734, Gafquat 755 or Gafquat 755N from Ashland Inc.

Polyquaternium-46 is the reaction product of vinylcaprolactam and vinylpyrrolidone with methylvinylimidazolium methosulfate and is available, for example, under the name Luviquat® Hold from BASF SE. Polyquaternium-46 is preferably used in an amount of 1 to 5% by weight—based on the total weight of the cosmetic composition. It is particularly preferred that polyquaternium-46 is used in combination with a cationic guar compound. In fact, it is highly preferred that polyquaternium-46 be used in combination with a cationic guar compound and polyquaternium-11.

Suitable anionic film-forming hydrophilic polymers can be, for example, acrylic acid polymers, which can be in uncrosslinked or crosslinked form. Corresponding products are sold commercially, for example, under the trade names Carbopol 980, 981, 954, 2984 and 5984 by the company Lubrizol or under the names Synthalen M and Synthalen K by the company 3V Sigma (The Sun Chemicals, Inter Resin).

Examples of suitable film-forming, hydrophilic polymers from the group of natural gums are xanthan gum, gellan gum, carob gum.

Examples of suitable film-forming, hydrophilic polymers from the group of polysaccharides are hydroxyethyl cellulose, hydroxypropyl cellulose, ethyl cellulose and carboxymethyl cellulose.

Suitable film-forming, hydrophilic polymers from the group of acrylamides are, for example, polymers prepared from monomers of (meth)acrylamido-C1-C4-alkyl sulfonic acid or salts thereof. Corresponding polymers may be selected from the polymers of polyacrylamidomethanesulfonic acid, polyacrylamidoethanesulfonic acid, polyacrylamidopropanesulfonic acid, poly2-acrylamido-2-methylpropanesulfonic acid, poly-2-methylacrylamido-2-methylpropanesulfonic acid, and/or poly-2-methylacrylamido-n-butanesulfonic acid.

Preferred polymers of poly(meth)arylamido-C1-C4-alkyl-sulfonic acids are crosslinked and at least 90% neutralized. These polymers can be crosslinked or non-crosslinked.

Cross-linked and fully or partially neutralized polymers of the poly-2-acrylamido-2-methylpropane sulfonic acid type are known under the INCI designations "ammonium polyacrylamido-2-methyl-propanesulfonate" or "ammonium polyacryldimethyltauramide".

Another preferred polymer of this type is the crosslinked poly-2-acrylamido-2methyl-propanesulfonic acid polymer sold by Clariant under the trade name Hostacerin AMPS, which is partially neutralized with ammonia.

In a further explicitly very particularly preferred embodiment, a process is wherein the agent (b) comprises at least one anionic, film-forming, polymer (b2).

In this context, the best results were obtained when the agent (b) comprises at least one film-forming polymer (b2) comprising at least one structural unit of formula (P-I) and at least one structural unit of formula (P-II) where M represents a hydrogen atom or ammonium (NH4), Sodium, potassium, ½ magnesium or

½ calcium.

In a further preferred embodiment, a process is wherein the agent (b) comprises at least one film-forming polymer (b2) comprising at least one structural unit of the formula (P-I) and at least one structural unit of the formula (P-II)

where
M represents a hydrogen atom or ammonium (NH4), Sodium, potassium, ½ magnesium or ½ Calcium stands.

When M represents a hydrogen atom, the structural unit of the formula (P-I) is based on an acrylic acid unit.

When M represents an ammonium counterion, the structural unit of formula (P-l) is based on the ammonium salt of acrylic acid.

When M represents a sodium counterion, the structural unit of formula (P-l) is based on the sodium salt of acrylic acid.

When M represents a potassium counterion, the structural unit of formula (P-l) is based on the potassium salt of acrylic acid.

If M stands for a half equivalent of a magnesium counterion, the structural unit of the formula (P-l) is based on the magnesium salt of acrylic acid.

If M stands for a half equivalent of a calcium counterion, the structural unit of the formula (P-l) is based on the calcium salt of acrylic acid.

The film-forming polymer or polymers (b2) are preferably used in certain ranges of amounts in the agent (b). In this context, it has proved particularly preferable for solving the problem as contemplated herein if the agent (b) comprises—based on the total weight of the agent (b)—one or more film-forming polymers (b2) in a total amount of from 0.1 to 18% by weight, preferably from 1 to 16% by weight, more preferably from 5 to 14.5% by weight and very particularly preferably from 8 to 12% by weight.

In a further preferred embodiment, a process is wherein the agent (b) comprises—based on the total weight of the agent (b)—one or more film-forming polymers (b2) in a total amount of from 0.1 to 18% by weight, preferably from 1 to 16% by weight, more preferably from 5 to 14.5% by weight and most preferably from 8 to 12% by weight.

Other Ingredients in Agents (a) and (b)

The previously described agents (a) and (b) may further include one or more optional ingredients.

It is particularly preferred that the agent (a) used in the dyeing process comprises at least one colorant compound (a2) selected from the group of pigments and/or direct dyes. The use of pigments has proved to be particularly preferable in this context.

In another very particularly preferred embodiment, a process is wherein the agent (a) comprises at least one colorant compound (a2) from the group comprising pigments. Pigments within the meaning of the present disclosure are colorant compounds which have a solubility in water at 25° C. of less than 0.5 g/L, preferably less than 0.1 g/L, still more preferably less than 0.05 g/L. Water solubility, for example, can be done using the method described below: 0.5 g of the pigment is weighed out in a beaker. A stir fish is added. Then one liter of distilled water is added. This mixture is heated to 25° C. for one hour with stirring on a magnetic stirrer. If undissolved components of the pigment are still visible in the mixture after this period, the solubility of the pigment is below 0.5 g/L. If the pigment-water mixture cannot be assessed visually due to the high intensity of the pigment, which may be finely dispersed, the mixture is filtered. If a portion of undissolved pigment remains on the filter paper, the solubility of the pigment is below 0.5 g/L.

Suitable pigments can be of inorganic and/or organic origin.

In a preferred embodiment, a process is wherein the agent (a) comprises at least one colorant compound (a2) from the group comprising inorganic and/or organic pigments. Preferred pigments are selected from synthetic or natural inorganic pigments. Inorganic pigments of natural origin can be produced, for example, from chalk, ocher, umber, green earth, burnt terra di siena or graphite. Furthermore, black pigments such as iron oxide black, colored pigments such as ultramarine or iron oxide red, and fluorescent or phosphorescent pigments can be used as inorganic pigments.

Particularly suitable are colored metal oxides, hydroxides and oxide hydrates, mixed-phase pigments, sulfur-comprising silicates, silicates, metal sulfides, complex metal cyanides, metal sulfates, chromates and/or molybdates. Particularly preferred pigments are black iron oxide (CI 77499), yellow iron oxide (CI 77492), red and brown iron oxide (CI 77491), manganese violet (CI 77742), ultramarines (sodium aluminum sulfosilicates, CI 77007, Pigment Blue 29), chromium oxide hydrate (CI77289), iron blue (ferric ferrocyanide, CI77510) and/or carmine (cochineal).

Also particularly preferred pigments are colored pearlescent pigments. These are usually mica-based and may be coated with one or more metal oxides. Mica belongs to the layer silicates. The main representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

Accordingly, a preferred process is wherein the agent (a) comprises at least one colorant compound (a2) from the group of pigments selected from the group of colored metal oxides, metal hydroxides, metal oxide hydrates, silicates, metal sulfides, complex metal cyanides, metal sulfates, bronze pigments and/or colored pigments based on natural mica coated with at least one metal oxide and/or a metal oxychloride.

In a further preferred embodiment, the process is wherein the agent (a) comprises at least one colorant compound (a2) from the group of pigments selected from pigments based on natural mica which are reacted with one or more metal oxides selected from the group of titanium dioxide (CI 77891), black iron oxide (CI 77499), yellow iron oxide (CI 77492), red and/or brown iron oxide (CI 77491, CI 77499), manganese violet (CI 77742), ultramarines (sodium aluminum sulfosilicates, CI 77007, Pigment Blue 29), chromium oxide hydrate (CI 77289), chromium oxide (CI 77288) and/or iron blue (ferric ferrocyanide, CI 77510).

Other suitable pigments are based on metal oxide-coated platelet-shaped borosilicates. These are coated with tin oxide, iron oxide(s), silicon dioxide and/or titanium dioxide, for example. Such borosilicate-based pigments are available, for example, under the name MIRAGE from Eckart or Reflecks from BASF SE.

Examples of particularly suitable pigments are commercially available under the trade names Rona®, Colorona®, Xirona®, Dichrona® and Timiron® from Merck, Ariabel® and Unipure® from Sensient, Prestige® from Eckart Cosmetic Colors, Flamenco®, Cellini®, Cloisonne®, Duocrome®, Gemtone®, Timica®, MultiReflections, Chione from BASF SE and Sunshine® from Sunstar.

Very particularly preferred pigments with the trade name Colorona® are, for example:

Colorona Copper, Merck, MICA, CI 77491 (IRON OXIDES)

Colorona Passion Orange, Merck, Mica, CI 77491 (Iran Oxides), Alumina

Colorona Patina Silver, Merck, MICA, CI 77499 (IRON OXIDES), CI 77891 (TITANIUM DIOXIDE)

Colorona RY, Merck, CI 77891 (TITANIUM DIOXIDE), MICA, CI 75470 (CARMINE)

Colorona Oriental Beige, Merck, MICA, CI 77891 (TITANIUM DIOXIDE), CI 77491 (IRON OXIDES) Colorona Dark Blue, Merck, MICA, TITANIUM DIOXIDE, FERRIC FERROCYANIDE Colorona Chameleon, Merck, CI 77491 (IRON OXIDES), MICA Colorona Aborigine Amber, Merck, MICA, CI 77499 (IRON OXIDES), CI 77891 (TITANIUM DIOXIDE) Colorona Blackstar Blue, Merck, CI 77499 (IRON OXIDES), MICA Colorona Patagonian Purple, Merck, MICA, CI 77491 (IRON OXIDES), CI 77891 (TITANIUM DIOXIDE), CI 77510 (FERRIC FERROCYANIDE)

Colorona Red Brown, Merck, MICA, CI 77491 (IRON OXIDES), CI 77891 (TITANIUM DIOXIDE) Colorona Russet, Merck, CI 77491 (TITANIUM DIOXIDE), MICA, CI 77891 (IRON OXIDES)

Colorona Imperial Red, Merck, MICA, TITANIUM DIOXIDE (CI 77891), D&C RED NO. 30 (CI 73360) Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491) Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES) Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (Iran oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iran oxides), Mica, CI 77891 (Titanium dioxide)
Colorona Bright Gold, Merck, Mica, CI 77891 (Titanium dioxide), CI 77491 (Iran oxides)
Colorona Blackstar Gold, Merck, MICA, CI 77499 (IRON OXIDES)
Colorona SynCopper, Merck, Synthetic Fluorphlogopite (and) Iran Oxides
Colorona SynBronze, Merck, Synthetic Fluorphlogopite (and) Iran Oxides Further particularly preferred pigments with the trade name Xirona® are, for example:
Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.
Xirona Le Rouge, Merck, Iran Oxides (and) Silica
In addition, particularly preferred pigments with the trade name Unipure® are, for example:
Unipure Red LC 381 EM, Sensient CI 77491 (Iran Oxides), Silica
Unipure Black LC 989 EM, Sensient, CI 77499 (Iran Oxides), Silica
Unipure Yellow LC 182 EM, Sensient, CI 77492 (Iran Oxides), Silica Also particularly preferred pigments with the trade name Flamenco® are, for example:
Flamenco® Summit Turquoise T30D, BASF, Titanium Dioxide (and) Mica
Flamenco® Super Violet 530Z, BASF, Mica (and) Titanium Dioxide In a further embodiment, the agent (a) used in the process may also contain one or more colorant compounds (a2) from the group of organic pigments.

The organic pigments are correspondingly insoluble organic dyes or colorants which may be selected, for example, from the group of nitroso, nitro-azo, xanthene, anthraquinone, isoindolinone, isoindoline, quinacridone, perinone, perylene, diketopyrrolopyorrole, indigo, thioindido, dioxazine and/or triarylmethane compounds.

Particularly suitable organic pigments are, for example, carmine, quinacridone, phthalocyanine, sorghum, blue pigments with the color index numbers CI 42090, CI 69800, CI 69825, CI 73000, CI 74100, CI 74160, yellow pigments with the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470 may be mentioned.

In a further particularly preferred embodiment, the process is wherein the composition (a) comprises at least one colorant compound (a2) from the group of organic pigments selected from the group of carmine, quinacridone, phthalocyanine, sorghum, blue pigments having the Color Index numbers CI 42090, CI 69800, CI 69825, CI 73000, CI 74100, CI 74160, yellow pigments with Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof.

The organic pigment can also be a colored coating. As contemplated herein, the term color varnish is understood to mean particles comprising a layer of absorbed dyes, the unit of particle and dye being insoluble under the above conditions. The particles may be, for example, inorganic substrates, which may be aluminum, silica, calcium borosilicate, calcium aluminum borosilicate, or aluminum.

Alizarin color varnish, for example, can be used as a color varnish.

Also, suitable colorant compounds (a2) from the group of pigments are inorganic and/or organic pigments modified with a polymer. The polymer modification can, for example, increase the affinity of the pigments to the respective material of the at least one layer. Other effect pigments can also be used as a further colorant compound (a2).

The further effect pigments may include, for example, pigments based on a lamellar substrate platelet, pigments based on lenticular substrate platelets, pigments based on substrate platelets comprising "vacuum metallized pigments" (VMP). In these effect pigments, the substrate platelets comprise a metal, preferably alumnium, or an alloy. Metal substrate platelet-based effect pigments preferably have a coating which, among other things, acts as a protective layer.

Suitable effect pigments include, for example, the pigments Alegrace® Marvelous, Alegrace© Gorgeous or Alegrace® Aurous from Schlenk Metallic Pigments.

Also, suitable effect pigments are the aluminum-based pigments of the SILVERDREAM series and the pigments of Eckart's VISIONAIRE series based on aluminum or on copper/zinc-comprising metal alloys.

Other suitable effect pigments are based on metal oxide-coated platelet-shaped borosilicates. These are coated with tin oxide, iron oxide(s), silicon dioxide and/or titanium dioxide, for example. Such borosilicate-based pigments are available, for example, under the name MIRAGE from Eckart or Reflecks from BASF SE.

In a further embodiment of the process, the agent (a) may also contain one or more colorant compounds from the group of organic pigments.

In a further particularly preferred embodiment, a process is wherein the agent (a) comprises at least one colorant compound (a2) from the group of organic pigments selected from the group of carmine, quinacridone, phthalocyanine, sorgho, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with color index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

Due to their excellent light and temperature stability, the use of the above pigments in agent (a) is particularly preferred. Furthermore, it is preferred if the pigments used have a certain particle size. On the one hand, this particle size leads to an even distribution of the pigments in the polymer film formed and, on the other hand, avoids a rough hair or skin feeling after application of the cosmetic product. It is therefore advantageous as contemplated herein if the at least one pigment has a mean particle size D50 of from 1 to 50 μm, preferably from 5 to 45 gm, preferably from 10 to 40 μm, from 14 to 30 μm. The average particle size D50 can be determined, for example, using dynamic light scattering (DLS).

In a further preferred embodiment, the process is wherein the agent (a) comprises—based on the total weight of the agent (a)—one or more coloring compound(s) (a2) in the form of pigments in a total amount of from 0.01 to 10% by weight, preferably from 0.1 to 8 wt. %, further preferred from 0.2 to 6 wt. % and very preferably from 0.5 to 4.5 wt. %.

As colorant compound(s) (a2), the agents (a) used in the process may also contain one or more direct dyes. Direct-acting dyes are dyes that draw directly onto the hair and do not require an oxidative process to form the color. Direct dyes are usually nitrophenylenediamines, nitroaminophenols, azo dyes, anthraquinones, triarylmethane dyes or indophenols.

The direct dyes in the sense of the present disclosure have a solubility in water (760 mmHg) at 25° C. of more than 0.5 g/L and are therefore not to be regarded as pigments. Preferably, the direct dyes in the sense of the present disclosure have a solubility in water (760 mmHg) at 25° C. of more than 1 g/L.

Direct dyes can be divided into anionic, cationic and nonionic direct dyes.

In a further preferred embodiment, the process is wherein the agent (a) further comprises as colorant compound (a2) at least one anionic, cationic and/or nonionic direct dye. In a further preferred embodiment, the process is wherein the agent (a) further comprises at least one colorant compound (a2) selected from the group of anionic, nonionic, and/or cationic direct dyes.

Suitable cationic direct dyes include Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76

Examples of nonionic direct dyes that can be used are nonionic nitro and quinone dyes and neutral azo dyes. Suitable nonionic direct dyes are those available under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)-amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

In the course of the work leading to the present disclosure, it has been found that dyeings of particularly high color intensity can be produced with agents (a) comprising at least one anionic direct dye.

In an explicitly quite particularly preferred embodiment, the process is therefore wherein the agent (a) further comprises at least one anionic direct dye as colorant compound (a2).

Anionic direct dyes are also called acid dyes. Acid dyes are direct dyes comprising at least one carboxylic acid group (—COOH) and/or one sulfonic acid group (—SO3H). Depending on the pH, the protonated forms (—COOH, —SO3H) of the carboxylic acid and sulfonic acid groups are in equilibrium with their deprotonated forms (—COO$^-$, —SO$_3^-$). As pH decreases, the proportion of protonated forms increases. If direct dyes are used in the form of their salts, the carboxylic acid groups or sulfonic acid groups are present in deprotonated form and are neutralized with corresponding stoichiometric equivalents of cations to maintain electroneutrality. The acid dyes can also be used in the form of their sodium salts and/or their potassium salts.

The acid dyes in the sense of the present disclosure have a solubility in water (760 mmHg) at 25° C. of more than 0.5 g/L and are therefore not to be regarded as pigments. Preferably, the acid dyes in the sense of the present disclosure have a solubility in water (760 mmHg) at 25° C. of greater than 1 g/L.

The alkaline earth salts (such as calcium salts and magnesium salts) or aluminum salts of acid dyes often have poorer solubility than the corresponding alkali salts. If the solubility of these salts is below 0.5 g/L (25° C., 760 mmHg), they do not fall under the definition of a direct dye.

A key feature of acid dyes is their ability to form anionic charges, with the carboxylic or sulfonic acid groups responsible for this usually being attached to various chromophore systems. Suitable chromophore systems can be found, for example, in the structures of nitrophenylenediamines, nitroaminophenols, azo dyes, anthraquinone dyes, triarylmethane dyes, xanthene dyes, rhodamine dyes, oxazine dyes, and/or indophenol dyes.

In the context of one embodiment, a process for dyeing keratinous material is thus preferred, which is wherein the agent (a) further comprises at least one anionic direct dye as the coloring compound (a2), which is selected from the group of the nitrophenylenediamines, the nitroaminophenols, the azo dyes, the anthraquinone dyes, the triarylmethane dyes, the xanthene dyes, the rhodamine dyes, the oxazine dyes and/or the indophenol dyes, the dyes from the abovementioned group each comprising at least one carboxylic acid group (—COOH), a sodium carboxylate group (—COONa), a potassium carboxylate group (—COOK), a sulfonic acid group (—SO3H), a sodium sulfonate group (—SO$_3$Na) and/or a potassium sulfonate group (—SO3K).

For example, one or more compounds from the following group can be selected as particularly well-suited acid dyes: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C. 29, Covacap Jaune W1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-naphthol orange, Orange II, CI 15510, D&C Orange 4, COLIPA no C015), Acid Orange 10 (C.1. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; no sodium salt; Brown No. 201; RESORCIN BROWN; ACID ORANGE 24; Japan Brown 201; D & C Brown No. 1), Acid Red 14 (C.1.14720), Acid Red 18 (E124, Red 18; CI 16255), Acid Red 27 (E 123, CI 16185, C-Red 46, Real Red D, FD&C Red No. 2, Food Red 9, Naphthol Red S), Acid Red 33 (Red 33, Fuchsia Red, D&C Red 33, CI 17200), Acid Red 35 (CI C.1.18065), Acid Red 51 (CI 45430, pyrosine B, tetraiodofluorescein, eosin J, lodeosin), Acid Red 52 (CI 45100, Food Red 106, Solar Rhodamine B, Acid Rhodamine B, Red no 106 Pontacyl Brilliant Pink), Acid Red 73 (CI 27290), Acid Red 87 (Eosin, CI 45380), Acid Red 92 (COLIPA no C53, CI 45410), Acid Red 95 (CI 45425, Erythtosine.Simacid Erythrosine Y), Acid Red 184 (CI 15685), Acid Red 195, Acid Violet 43 (Jarocol Violet 43, Ext. D&C Violet no 2, C.1. 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido Blue AE, Erioglaucin A, CI 42090, C.1. Food Blue 2), Acid Blue 62 (CI 62045), Acid Blue 74 (E 132, CI 73015), Acid Blue 80 (CI 61585), Acid Green 3 (CI 42085, Food green), Acid Green 5 (CI 42095), Acid Green 9 (C.1.42100), Acid Green 22 (C.1.42170), Acid Green 25 (CI 61570, Japan Green 201, D&C Green No. 5), Acid Green 50 (Brilliant Acid Green BS, C.1. 44090, Acid Brilliant Green BS, E 142), Acid Black 1 (Black n° 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The water solubility of anionic direct dyes can be determined, for example, in the following way. 0.1 g of the anionic direct dye is added to a beaker. A stir fish is added. Then 100 ml of water is added. This mixture is heated to 25° C. on a magnetic stirrer while stirring. It is stirred for 60 minutes. The aqueous mixture is then visually assessed. If undissolved residues are still present, the amount of water is increased—for example in steps of 10 ml. Water is added until the amount of dye used has completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml of water at 25° C., the solubility of the dye is 1 g/L.

Acid Yellow 1 is named 8-hydroxy-5,7-dinitro-2-naphthalenesulfonic acid disodium salt and has a solubility in water of at least 40 g/L (25° C.).

Acid Yellow 3 is a mixture of the sodium salts of mono- and disulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, and its water solubility is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is readily soluble in water at 25° C.

Acid Orange 7 is the sodium salt of 4-[(2-hydroxy-1-naphthyl)azo]benzenesulfonate. Its solubility in water is more than 7 g/L (25° C.). Acid Red 18 is the trisodium salt of 7-hydroxy-8-[(E)-(4-sulfonato-1-naphthyl)-diazenyl)]-1,3-naphthalenedisulfonate and has a very high water solubility of more than 20% by weight. Acid Red 33 is the disodium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is reported to be greater than 10 g/L (25° C.).

Acid Blue 9 is the disodium salt of 2-({4-[N-ethyl(3-sulfonatobenzyl]amino]phenyl} {4-[(N-ethyl(3-sulfonatobenzyl)imino]-2,5-cyclohexadien-1-ylidene}methyl)-benzenesulfonate and has a water solubility greater than 20% by weight (25° C.).

A very particularly preferred process is therefore wherein the agent (a) comprises at least one first coloring compound (a2) from the group of anionic direct dyes selected from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct dye(s), in particular the anionic direct dyes, can be used in different amounts in the medium (a) depending on the desired color intensity. Particularly good results were obtained when the agent (a) comprises—based on its total weight—one or more direct dyes (a2) in a total amount of from 0.01 to 10% by weight, preferably from 0.1 to 8% by weight, more preferably from 0.2 to 6% by weight and very particularly preferably from 0.5 to 4.5% by weight.

In a further preferred embodiment, the process is wherein the agent (a)—based on the total weight of the agent (a)—further comprises one or more direct dyes as colorant compound (a2) in a total amount of from 0.01 to 10% by weight, preferably from 0.1 to 8% by weight, more preferably from 0.2 to 6% by weight and most preferably from 0.5 to 4.5% by weight.

The agents may additionally contain one or more surfactants. The term surfactants are used to describe surface-active substances. A distinction is made between anionic surfactants comprising a hydrophobic residue and a negatively charged hydrophilic head group, amphoteric surfactants, which carry both a negative and a compensating positive charge, cationic surfactants, which have a positively charged hydrophilic group in addition to a hydrophobic residue, and nonionic surfactants, which have no charges but strong dipole moments and are strongly hydrated in aqueous solution.

The term zwitterionic surfactants is used to describe surface-active compounds that carry at least one quaternary ammonium group and at least one —COO$^{(+)}$— or —SO$_3^{(+)}$— group in the molecule. Particularly suitable zwitterionic surfactants are the so-called betaines such as the N-alkyl-N,N-dimethylammonium glycinates, for example cocoalkyl dimethylammonium glycinate, N-acylaminopropyl-N,N-dimethylammonium glycinate, for example the cocoacylaminopropyl-dimethylammonium glycinate, and 2-alkyl-3-carboxymethyl-3-hydroxyethyl-imidazolines each having from 8 to 18 carbon atoms in the alkyl or acyl group and the Cocosacylaminoethylhydroxyethylcarboxymethylglycinate. A preferred zwitterionic surfactant is the fatty acid amide derivative known under the INCI designation Cocamidopropyl Betaine.

Ampholytic surfactants are surface-active compounds which, in addition to a $C_8$-$C_{24}$-Alkyl or acyl group in the molecule, at least one free amino group and at least one —COOH or —SO$_3$H group and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having about 8 to 24 carbon atoms in the alkyl group. Typical examples of amphoteric or zwitterionic surfactants are alkyl betaines, alkylamidobetaines, amino propionates, aminoglycinates, imidazolinium betaines and sulfobetaines.

Particularly preferred ampholytic surfactants are N-cocosalkylaminopropionate, cocosacylaminoethylaminopropionate and C12-$C_{18}$-acylsarcosine.

The agents may also additionally contain at least one nonionic surfactant. Suitable nonionic surfactants are alkyl polyglycosides as well as alkylene oxide addition products to fatty alcohols and fatty acids, each with 2 to 30 moles of ethylene oxide per mole of fatty alcohol or fatty acid, respectively. Preparations with good properties are also obtained if they contain, as nonionic surfactants, fatty acid esters of ethoxylated glycerol reacted with at least 2 moles of ethylene oxide.

Furthermore, the agents may also additionally contain at least one cationic surfactant. Cationic surfactants are surfactants, i.e., surface-active compounds, each with one or more positive charges. Cationic surfactants contain only positive charges. Typically, these surfactants are composed of a hydrophobic moiety and a hydrophilic head group, with the hydrophobic moiety usually comprising a hydrocarbon backbone (e.g., comprising one or two linear or branched alkyl chains), and the positive charge(s) located in the hydrophilic head group. Examples of cationic surfactants are quaternary ammonium compounds which may carry one or two alkyl chains with a chain length of 8 to 28 carbon atoms as hydrophobic radicals, quaternary phosphonium salts substituted by one or more alkyl chains having a chain length of 8 to 28 carbon atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case, for example, with esterquats. The cationic surfactants are used in a total amount of 0.1 to 45% by weight, preferably 1 to 30% by weight and very preferably 1 to 15% by weight—based on the total weight of the respective agent.

Furthermore, the agents may also contain at least one anionic surfactant. Anionic surfactants are surface-active agents with exclusively anionic charges (neutralized by a corresponding counter cation). Examples of anionic surfactants are fatty acids, alkyl sulfates, alkyl ether sulfates and ether carboxylic acids with 12 to 20 C atoms in the alkyl group and up to 16 glycol ether groups in the molecule.

The anionic surfactants are used in a total amount of 0.1 to 45% by weight, preferably 1 to 30% by weight and very preferably 1 to 15% by weight—based on the total weight of the respective agent.

To adjust the desired pH, agents (a) and (b) may also contain at least one alkalizing agent and/or acidifying agent. The pH values for the purposes of the present disclosure are pH values measured at a temperature of 22° C.

As alkalizing agents, agents (a) and (b) may contain, for example, ammonia, alkanolamines and/or basic amino acids.

The alkanolamines that can be used in the compositions are preferably selected from primary amines having a C2-$C_6$-Alkyl backbone bearing at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol.

Particularly preferred alkanolamines are selected from 2-aminoethan-1-ol and/or 2-amino-2-methylpropan-1-ol. A particularly preferred embodiment is therefore wherein an agent (a) and/or (b) comprises as alkalizing agent an alkanolamine selected from 2-aminoethan-1-ol and/or 2-amino-2-methylpropan-1-ol.

For the purposes of the present disclosure, an amino acid is an organic compound comprising in its structure at least one protonatable amino group and at least one —COOH or one —SO$_3$H group. Preferred amino acids are aminocarboxylic acids, in particular α-(alpha)-

Aminocarboxylic acids and w-aminocarboxylic acids, with a-aminocarboxylic acids being particularly preferred.

As contemplated herein, basic amino acids are those amino acids which have an isoelectric point pI greater than 7.

Basic α-aminocarboxylic acids contain at least one asymmetric carbon atom. In the context of the present disclosure, both possible enantiomers can be used equally as specific compounds or also mixtures thereof, as racemates. However, it is particularly advantageous to use the naturally preferable isomeric form, usually in L-configuration.

The basic amino acids are preferably selected from the group formed by arginine, lysine, ornithine and histidine, particularly preferably arginine and lysine. In a further particularly preferred embodiment, an agent is therefore wherein the alkalizing agent is a basic amino acid from the group comprising arginine, lysine, ornithine and/or histidine.

In addition, the agents (a) and/or (b) may contain further alkalizing agents, in particular inorganic alkalizing agents. Applicable inorganic alkalizing agents are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Very particularly preferred alkalizing agents are ammonia, 2-aminoethan-1-ol (monoethanolamine), 3-aminopropan-1-ol, 4-aminobutan-1-ol, 5-aminopentan-1-ol, 1-amino-propan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Acidifiers familiar to the skilled person are, for example, organic acids, such as citric acid, acetic acid, maleic acid, lactic acid, malic acid or tartaric acid, and dilute mineral acids, such as hydrochloric acid, sulfuric acid or phosphoric acid.

Agent (a) and/or agent (b) may remotely contain matting agent. Suitable matting agents include, for example, (modified) starches, waxes, talc and/or (modified) silicas. The amount of matting agent is preferably between 0.1 and 10% by weight based on the total amount of agent (a) or agent (b). Preferably, agent (b) comprises a matting agent.

The agents (a) and/or (b) may also contain other active ingredients, auxiliaries and additives, such as solvents, fatty components such as the $C_8$-$C_{30}$ fatty acid triglycerides, $C_8$-$C_{30}$ fatty acid monoglycerides, $C_8$-$C_{30}$ fatty acid diglycerides and/or hydrocarbons; polymers; structuring agents such as glucose or sodium chloride, hair conditioning compounds such as phospholipids, for example lecithin and cephalins; Perfume oils, dimethyl isosorbide and cyclodextrins; fiber structure improving agents, in particular mono-, di- and oligosaccharides such as glucose, galactose, fructose, fructose and lactose; Dyes for coloring the product; anti-dandruff active ingredients such as piroctone olamine, zinc omadine and climbazole; amino acids and oligopeptides; protein hydrolysates on animal and/or vegetable basis, as well as in the form of their fatty acid condensation products or optionally anionically or cationically modified derivatives; vegetable oils; light stabilizers and UV blockers; active substances such as panthenol, pantothenic acid, pantolactone, allantoin, pyrrolidinonecarboxylic acids and their salts, and bisabolol; Polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; Fats and waxes such as fatty alcohols, beeswax, montan wax and kerosenes; swelling and penetrating agents such as glycerol, propylene glycol mono-ethyl ether, carbonates, hydrogen carbonates, guanidines, ureas and primary, secondary and tertiary phosphates; Opacifiers such as latex, styrene/PVP and styrene/acrylamide copolymers; pearlescent agents such as ethylene glycol mono- and distearate and PEG-3 distearate; and blowing agents such as propane-butane mixtures, N2O, dimethyl ether, CO2 and air.

The selection of these other substances will be made by the skilled person according to the desired properties of the agents. Regarding further optional components as well as the quantities of these components used, reference is expressly made to the relevant manuals known to the skilled person. The additional active ingredients and auxiliaries are preferably used in the agents (a) and/or (b) in amounts of from 0.0001 to 25% by weight in each case, from 0.0005 to 15% by weight, based on the total weight of the respective agent.

Process for Dyeing Keratinous Materials

In the process, agents (a) and (b) are applied to the keratinous materials, especially human hair. Thus, agents (a) and (b) are the ready-to-use means. Agents (a) and (b) are different from each other.

Agents (a) and (b) can in principle be applied simultaneously or successively, with successive application being preferred.

The best results were obtained when agent (a) was applied to the keratinous materials as a pretreatment agent and then agent (b) was applied as a coloring agent.

Quite particularly preferred, therefore, is a process for dyeing keratinous material, in particular human hair, comprising the following steps in the order indicated:
  in a first step, applying an agent (a) to the keratinous material, the agent (a) comprising at least one organic silicon compound (a1), and
  in a second step, applying an agent (b) to the keratinous material, the agent comprising (b): (b1) at least one color-imparting compound comprising at least one effect pigment comprising α) a substrate platelet comprising synthetic mica, and ß) a coating comprising at least a first metal oxide (hydrate) layer, and (b2) at least one film-forming polymer.

Moreover, to impart a high leaching resistance to the dyed keratinous material over a longer period, agents (a) and (b) are particularly preferably applied within one and the same dyeing process, which means that there is a period of a maximum of several hours between the application of agents (a) and (b).

In a further preferred embodiment, the method is wherein the agent (a) is applied first and then the agent (b) is applied, the time between the application of the agents (a) and (b) being at most 24 hours, preferably at most 12 hours and particularly preferably at most 6 hours. In the process, the keratinous materials, in particular human hair, are first treated with agent (a).

A characteristic feature of the pretreatment agent (a) is its content of at least one reactive organic silicon compound. The reactive organic silicon compound(s) (a1) functionalize the hair surface as soon as they meet it. In this way, a first film is formed. In the second step of the process, a coloring agent (b) is now applied to the hair. During application of the colorant (b), the colorant compounds interact with the film formed by the organosilicon compounds and are thus bound to the keratinous materials.

In a particularly preferred embodiment of the process, the agent (a) comprises a color-imparting compound (a2) in addition to the reactive organic silicon compound(s) (a1). In this way, an initial colored film is formed on the keratinous material upon contact. In the second step of the process, agent (b) is applied to the keratinous material, which comprises an effect pigment as color-imparting compound (b1). During the application of agent (b), the colorant compounds (b1) interact with the film formed by the organosilicon compounds (a1) and colored with the colorant compounds (a2). In this way, the colorant compounds (b1) are bound to the keratinous material and, together with the colorant compounds (a2), produce particularly intense and resistant effect colorations.

In a further embodiment, a method comprising the following steps in the order indicated is particularly preferred
(1) Application of the agent (a) on the keratinous material,
(2) Allowing the agent (a) to act for a period of 10 seconds to 10 minutes, preferably from 10 seconds to 5 minutes,
(3) if necessary, rinsing the keratinous material with water,
(4) Application of the agent (b) on the keratinous material,
(5) Allowing the agent (b) to act for a period of from 30 seconds to 30 minutes, preferably from 30 seconds to 10 minutes, and
(6) Rinse the keratinous material with water.

As contemplated herein, the rinsing of the keratinous material with water in steps (3) and (6) of the process is understood to mean that only water is used for the rinsing process, without the use of any other agents different from agents (a) and (b).

In step (1), agent (a) is first applied to the keratinous materials, in particular human hair.

After application, agent (a) is allowed to act on the keratinous materials. In this context, exposure times of 10 seconds to 10 minutes, preferably 20 seconds to 5 minutes and most preferably 30 seconds to 2 minutes to the keratinous materials, to human hair, have proven to be particularly advantageous.

In a preferred embodiment of the process, the agent (a) can now be rinsed from the keratinic materials before the agent (b) is applied to the hair in the subsequent step.

Colorings with equally good wash fastness were obtained when agent (b) was applied to the keratinous materials that were still exposed to agent (a).

In step (4), agent (b) is now applied to the keratinous materials. After application, the agent (b) is now left to act on the hair.

Even with a short contact time of the agent (b), the process allows the production of dyeings with particularly good intensity and wash fastness. Exposure times of 10 seconds to 10 minutes, preferably of 20 seconds to 5 minutes and very preferably of 30 seconds to 3 minutes on the keratinous materials, especially on human hair, have proven to be particularly beneficial.

In step (6), the agent (b) (and any agent (a) still present) is now rinsed out of the keratinous material with water.

Multicomponent Packaging Unit (Kit-of-Parts)

In the process, agents (a) and (b) are applied to the keratinous materials, i.e., the two agents (a) and (b) are respectively the ready-to-use agents.

To increase user convenience, the user is preferably provided with all the necessary means in the form of a multi-component packaging unit (kit-of-parts).

A second object of the present disclosure is therefore a multi-component packaging unit (kit-of-parts) for dyeing keratinous material, comprising separately prepared
a first container comprising an agent (a), the agent (a) comprising at least one organic silicon compound (a1), and
a second container comprising an agent (b), wherein the agent comprises (b):
(b1) at least one color-imparting compound comprising at least one effect pigment comprising α) a substrate platelet comprising synthetic mica, and ß) a coating comprising at least a first metal oxide (hydrate) layer, and (b2) at least one film-forming polymer.

The organic silicon compounds included in agent (a) of the kit correspond to the organic silicon compounds that were also used in agent (a) of the previously described process. The colorant compounds from the group of effect pigments comprising α) a substrate platelet comprising synthetic mica, and ß) a coating comprising at least a first metal oxide (hydrate) layer included in agent (b) of the kit correspond to the colorant compounds from the group of effect pigments comprising α) a substrate platelet comprising synthetic mica, and ß) a coating comprising at least a first metal oxide (hydrate) layer, which were also used in agent (b) of the process described above.

Agent (a) comprises, with the organic silicon compound (s), a class of reactive compounds capable of undergoing hydrolysis and/or oligomerization and/or polymerization in the presence of water as previously described. As a result of their high reactivity, these organic silicon compounds form a film on the keratinous material.

To avoid premature hydrolysis, oligomerization and/or polymerization, it may be preferable to prepare the ready-to-use agent (a) only shortly before use.

In a further preferred embodiment, a multi-component kit-of-parts for dyeing keratinous material comprising separately prepared
a first container comprising an agent (a'), wherein the agent (a') comprises at least one organic silicon compound,
a second container comprising an agent (a"), the agent (a") comprising water, and
a third container comprising an agent (b), wherein the agent comprises (b):
(b1) at least one color-imparting compound comprising at least one effect pigment comprising α) a substrate platelet comprising synthetic mica, and ß) a coating comprising at least a first metal oxide (hydrate) layer, and (b2) at least one film-forming polymer.

To be able to provide a formulation that is as stable as possible in storage, the agent (a') itself is preferably formulated to be low in water or water-free.

In a preferred embodiment, a multicomponent packaging unit (kit-of-parts) is wherein the agent (a')—based on the total weight of the agent (a')—has a water content of less than 10% by weight, preferably less than 5% by weight, more preferably less than 1% by weight, even more preferably less than 0.1% by weight and very particularly preferably less than 0.01% by weight.

The agent (a") comprises water. In a preferred embodiment, a multicomponent packaging unit (kit-of-parts) is wherein the agent (a")—based on the total weight of the agent (a")—has a water content of from 15 to 100% by weight, preferably from 35 to 100% by weight, more preferably from 55 to 100% by weight, still more preferably from 65 to 100% by weight and very particularly preferably from 75 to 100% by weight.

Within this embodiment, the ready-to-use agent (a) is now prepared by mixing agents (a') and (a").

For example, the user can first mix or spill the agent (a') comprising the organic silicon compound(s) with the water-comprising agent (a"). The user can now apply this mixture of (a') and (a")—either directly after its preparation or after a short reaction time of 10 seconds to 20 minutes—to the keratinous materials. Subsequently, the user can apply the agent (b) as previously described.

In this embodiment of the multicomponent packaging unit, it may be preferred that the agent (a″) further comprises at least one color-imparting compound (a2). This is preferably selected from the group of colored metal oxides, metal hydroxides, metal oxide hydrates, silicates, metal sulfides, complex metal cyanides, metal sulfates, bronze pigments and/or colored pigments based on natural mica coated with at least one metal oxide and/or a metal oxychloride.

In a further preferred embodiment, a multi-component kit-of-parts for dyeing keratinous material comprising separately prepared
- a first container comprising an agent (a'), wherein the agent (a') comprises at least one organic silicon compound,
- a second container comprising an agent (a″), the agent (a″) comprising water and at least one colorant compound (a2), and
- a third container comprising an agent (b), wherein the agent comprises (b):

(b1) at least one color-imparting compound comprising at least one effect pigment comprising α) a substrate platelet comprising synthetic mica, and ß) a coating comprising at least a first metal oxide (hydrate) layer, and (b2) at least one film-forming polymer.

Alternatively, multicomponent packaging unit may further comprise an agent (a‴) comprising at least one coloring compound (a2).

Within this embodiment, the ready-to-use agent (a) is now prepared by mixing agents (a'), (a″) and (a‴). Preferably, the agent (a‴) further comprises a solvent. It may also be preferable to prepare the ready-to-use agent (b) shortly before use. In a further advantageous embodiment, the ready-to-use agent (b) is prepared by mixing an agent (b') and an agent (b″).

In a further preferred embodiment, a multi-component kit-of-parts for dyeing keratinous material comprising separately prepared
- a first container comprising an agent (a'), wherein the agent (a') comprises at least one organic silicon compound,
- a second container comprising an agent (a″), wherein the agent (a″) comprises water,
- a third container comprising an agent (b'), said agent comprising (b):

(b1) at least one coloring compound comprising at least one effect pigment comprising α) a substrate platelet comprising synthetic mica, and ß) a coating comprising at least a first metal oxide (hydrate) layer, and
- a fourth container comprising an agent (b″), wherein the agent comprises (b″): (b2) at least one film-forming polymer.

With respect to the further preferred embodiments of the multicomponent packaging unit mutatis mutantis what has been said about the process.

Examples

1. Formulations

The following formulations were prepared (unless otherwise stated, all figures are in wt. %)

| Pretreatment agent, agent (a) | |
|---|---|
| (3-Aminopropyl)triethoxysilane | 2.0 |
| Methyltrimethoxysilane | 7.0 |

-continued

| Pretreatment agent, agent (a) | |
|---|---|
| Ammonia/citric acid | ad pH 9.5 |
| Water | ad 100 |

The silanes were mixed with a portion of water, this mixture was left for 30 minutes. Then the pH was adjusted to the desired value by adding citric acid/ammonia. Water was then added to make up to 100 g.

| Dye, agent (b) | |
|---|---|
| Timiron ® SynWhite Satin (ex Merck) | 1 |
| PVP K 30 (Ashland, ISP, | 4.5 |
| Dermacryl 79 (Akzo Nobel, Acrylates/Octylacrylamide Copolymer, | 4.5 |
| Ammonia (25% aqueous solution) | ad pH 10 |
| Water | ad 100 |

2. Application

One strand of hair (Kerling, Euronatural hair white) was dipped into the medium (a) and left in it for 1 minute. Then, excess agent (a) was stripped from each strand of hair. Each strand of hair was briefly washed with water. Excess water was brushed from each strand of hair.

Subsequently, the hair strands were each dipped in the agent (b) and left in it for 1 minute. Then, excess agent (b) was stripped from each strand of hair. Each strand of hair was briefly washed with water. Excess water was brushed from each strand of hair.

Subsequently, the strands were visually evaluated.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for dyeing keratinous material, comprising the following steps:
    applying a first agent (a) to the keratinous material, wherein the first agent (a) comprises:
    (a1) at least one organic silicon compound of the formula (I) and at least one organic silicon compound of the formula (IV),
    where in the organic silicon compound of the formula (I):

$$R_1R_2N\text{-}L\text{-}Si(OR_3)_a(R_4)_b \qquad (I),$$

$R_1$, $R_2$ independently represent a hydrogen atom or a $C_1$-$C_6$-Alkyl group,
    L represents a linear or branched divalent $C_1$-$C_{20}$-alkylene group,
    $R_3$ represents a hydrogen atom or for a $C_1$-$C_6$-Alkyl group, R$_4$ represents a C$_1$-C$_6$-Alkyl group,
a represents an integer from 1 to 3, and
b stands for the integer 3−a, and
where in the organic silicon compound of the formula (IV):

R$_9$ represents a C$_1$-C$_{18}$-alkyl group,
R$_{10}$ represents a hydrogen atom or a C$_1$-C$_6$-alkyl group,
R$_{11}$ represents a C$_1$-C$_6$-alkyl group,
k is an integer from 1 to 3, and
m stands for the integer 3−k, and
applying a second agent (b) to the keratinous material, wherein the second agent (b) comprises:
(b1) at least one colorant compound comprising at least one effect pigment comprising a substrate platelet comprising synthetic mica, and a coating comprising at least a first metal oxide (hydrate) layer, and
(b2) at least one film-forming polymer.

2. The method according to claim 1, wherein
R$_1$ and R$_2$ each represent a hydrogen atom,
L represents a propylene group (—CH$_2$—CH$_2$—CH$_2$—) or an ethylene group (—CH$_2$—CH$_2$—),
R3 represents a hydrogen atom, an ethyl group, or a methyl group,
R4 represents a methyl group or an ethyl group,
a represents the number 3, and
b represents the number 0.

3. The method of claim 1, wherein the first agent (a) further comprises at least one organic silicon compound of the formula (II)

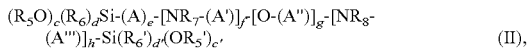

where
R$_5$, R$_5$', R$_5$" independently represent a hydrogen atom or a C$_1$-C$_6$-Alkyl group,
R$_6$, R$_6$' and R$_6$" independently represent a C$_1$-C6-Alkyl group,
A, A', A", A'" and A"" independently represent a linear or branched divalent C$_1$-C$_{20}$-alkylene group,
R$_7$ and R$_8$ independently represent a hydrogen atom, a C$_1$-C$_6$ alkyl group, a hydroxy-C$_1$-C$_6$ alkyl group, a C2-C$_6$-Alkenyl group, an amino-C$_1$-C$_6$-alkyl group or a group of the formula (III):

where
c represents an integer from 1 to 3,
d represents the integer 3−c,
c' represents an integer from 1 to 3,
d' represents the integer 3−c',
c" represents an integer from 1 to 3,
d" represents the integer 3−c",
e represents 0 or 1,
f represents 0 or 1,
g represents 0 or 1,
h represents 0 or 1,
wherein at least one of the residues from e, f, g and h is different from 0.

4. The method of claim 1, wherein
R$_1$ and R$_2$ each represent a hydrogen atom,
L represents a linear, divalent C$_1$-C$_6$ alkylene group,
R3 represents a hydrogen atom, an ethyl group, or a methyl group,
R4 represents a methyl group or an ethyl group,
a represents the number 3, and
b represents the number 0.

5. The method of claim 1, wherein the first agent (a) comprises at least one organic silicon compound of formula (I) selected from the group consisting of:
(3-Aminopropyl)triethoxysilane;
(3-Aminopropyl)trimethoxysilane;
1-(3-aminopropyl)silanetriol;
(2-Aminoethyl)triethoxysilane;
(2-Aminoethyl)trimethoxysilane;
1-(2-aminoethyl)silanetriol;
(3-Dimethylaminopropyl)triethoxysilane;
(3-Dimethylaminopropyl)trimethoxysilane;
1-(3-Dimethylaminopropyl)silanetriol;
(2-dimethylaminoethyl)triethoxysilane;
(2-dimethylaminoethyl)trimethoxysilane;
1-(2-dimethylaminoethyl)silanetriol; and
Mixtures thereof.

6. The method of claim 3, wherein the first agent (a) further comprises at least one organic silicon compound of the formula (II),

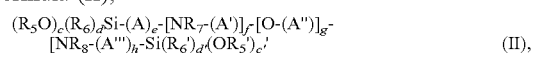

where
e and f both represent the number 1,
g and h both represent the number 0,
A and A' independently represent a linear, divalent C$_1$-C$_6$ alkylene group, and
R$_7$ represents a hydrogen atom, a methyl group, a 2-hydroxyethyl group, a 2-alkenyl group, a 2-aminoethyl group or a group of formula (III).

7. The method of claim 3, wherein the at least one organic silicon compound of formula (II) is selected from the group consisting of:
3-(Trimethoxysilyl)-N-[3-(trimethoxysilyl)propyl]-1-propanamine;
3-(Triethoxysilyl)-N-[3-(triethoxysilyl)propyl]-1-propanamine;
N-methyl-3-(trimethoxysilyl)-N-[3-(trimethoxysilyl)propyl]-1-propanamine;
N-methyl-3-(triethoxysilyl)-N-[3-(triethoxysilyl)propyl]-1-propanamine;
2-[Bis[3-(trimethoxysilyl)propyl]amino]ethanol;
2-[Bis[3-(triethoxysilyl)propyl]amino]ethanol;
3-(Trimethoxysilyl)-N,N-bis[3-(trimethoxysilyl)propyl]-1-propanamine;
3-(triethoxysilyl)-N,N-bis[3-(triethoxysilyl)propyl]-1-propanamine;
N1,N1-bis[3-(trimethoxysilyl)propyl]-1,2-ethanediamine;
N1,N1-bis[3-(triethoxysilyl)propyl]-1,2-ethanediamine;
N,N-bis[3-(trimethoxysilyl)propyl]-2-propen-1-amine;
N,N-bis[3-(triethoxysilyl)propyl]-2-propen-1-amine; and
Mixtures thereof.

8. The method of claim 1, wherein the at least one organic silicon compound of formula (IV) is selected from the group consisting of:
Methyltrimethoxysilane;
Methyltriethoxysilane;
Ethyltrimethoxysilane;
Ethyltriethoxysilane;
Propyltrimethoxysilane;
Propyltriethoxysilane;
Hexyltrimethoxysilane;
Hexyltriethoxysilane;
Octyltrimethoxysilane;
Octyltriethoxysilane;

Dodecyltrimethoxysilane;
Dodecyltriethoxysilane;
Octadecyltrimethoxysilane;
Octadecyltriethoxysilane; and
Mixtures thereof.

9. The method of claim 1, wherein the first metal oxide (hydrate) layer comprises titanium dioxide ($TiO_2$).

10. The method of claim 1, wherein the coating further comprises a second metal oxide (hydrate) layer.

11. The method of claim 10, wherein the second metal oxide (hydrate) layer is a metal oxide (hydrate) selected from the group consisting of tin oxide ($SnO_2$), silicon oxide ($SiO_2$), aluminum oxide ($Al_2O_3$), Iron oxide ($Fe_2O_3$ and/or $Fe_3O_4$), and mixtures thereof.

12. The method of claim 10, wherein the second metal oxide (hydrate) layer comprises tin oxide ($SnO_2$).

13. The method of claim 1, wherein the first agent (a) further comprises at least one coloring compound (a2), which is selected from the group of colored metal oxides, metal hydroxides, metal oxide hydrates, silicates, metal sulfides, complex metal cyanides, metal sulfates, bronze pigments, colored pigments based on mica coated with at least one metal oxide, and colored pigments based on mica coated with a metal oxychloride.

14. A multi-component packaging unit (kit-of-parts) for dyeing keratinous material, comprising separately assembled
a first container comprising a first agent (a), wherein the first agent (a) comprises at least one organic silicon compound of the formula (I) and at least one organic silicon compound of the formula (IV),
where in the organic silicon compound of the formula (I):

$$R_1R_2N\text{-}L\text{-}Si(OR_3)_a(R_4)_b \qquad (I),$$

$R_1$, $R_2$ independently represent a hydrogen atom or a $C_1$-$C_6$-Alkyl group,
L represents a linear or branched divalent $C_1$-$C_{20}$-alkylene group,
$R_3$ represents a hydrogen atom or for a $C_1$-$C_6$-Alkyl group,
$R_4$ represents a $C_1$-$C_6$-Alkyl group,
a represents an integer from 1 to 3, and
b stands for the integer 3−a, and
where in the organic silicon compound of the formula (IV):

$$R_9Si(OR_{10})_k(R_{11})_m \qquad (IV),$$

$R_9$ represents a $C_1$-$C_{18}$-alkyl group,
$R_{10}$ represents a hydrogen atom or a $C_1$-$C_6$-alkyl group,
$R_{11}$ represents a $C_1$-$C_6$-alkyl group,
k is an integer from 1 to 3, and
m stands for the integer 3−k, and
a second container containing a second agent (b), wherein the second agent (b) comprises: (b 1) at least one colorant compound comprising at least one effect pigment comprising a substrate platelet comprising synthetic mica, and a coating comprising at least a first metal oxide (hydrate) layer, and
(b2) at least one film-forming polymer.

* * * * *